US005583015A

United States Patent [19]

Hafner et al.

[11] Patent Number: 5,583,015
[45] Date of Patent: Dec. 10, 1996

[54] PROCESS FOR PRODUCTION OF AVERMECTINS

[75] Inventors: Edmund W. Hafner, East Lyme, Conn.; Kelvin S. Holdom, Ramsgate, England; S. Edward Lee, Waterford, Conn.

[73] Assignee: Pfizer Inc., New York, N.Y.

[21] Appl. No.: 323,163

[22] Filed: Oct. 14, 1994

Related U.S. Application Data

[60] Continuation of Ser. No. 60,452, May 11, 1993, abandoned, which is a division of Ser. No. 660,912, Feb. 27, 1991, Pat. No. 5,238,848, which is a continuation of Ser. No. 107,825, Sep. 13, 1987, abandoned, which is a continuation-in-part of Ser. No. 6,512, Jan. 23, 1987, abandoned.

[51] Int. Cl.$^6$ .............. C12P 19/62; C12P 17/18; C12N 1/20
[52] U.S. Cl. .............. 435/76; 435/75; 435/119; 435/244; 435/253.5; 435/172.1; 435/172.2; 536/7.1
[58] Field of Search .............. 435/119, 172.1, 435/172.2, 75, 76, 253.5, 244; 536/7.1

[56] References Cited

U.S. PATENT DOCUMENTS

| | | | |
|---|---|---|---|
| 4,134,973 | 1/1979 | Fisher et al. | 424/180 |
| 4,156,720 | 5/1979 | Fisher et al. | 424/180 |
| 4,199,569 | 4/1980 | Chabala et al. | 424/180 |
| 4,285,963 | 8/1981 | Arison et al. | 424/279 |
| 4,310,519 | 1/1982 | Albers-Schonberg et al. | 424/181 |
| 4,328,335 | 5/1982 | Mrozik | 536/7.1 |
| 4,333,925 | 6/1982 | Buhs et al. | 536/7.1 |
| 4,378,353 | 3/1983 | Goegelman et al. | 424/181 |
| 4,423,209 | 12/1983 | Mrozik | 536/7.1 |
| 4,429,042 | 1/1984 | Albers-Schonberg et al. | 435/119 |
| 4,831,016 | 5/1989 | Mrozik | 514/30 |

FOREIGN PATENT DOCUMENTS

| | | |
|---|---|---|
| 1689 | 5/1979 | European Pat. Off. . |
| 2615 | 6/1979 | European Pat. Off. . |
| 7812 | 2/1980 | European Pat. Off. . |
| 214731 | 3/1987 | European Pat. Off. . |
| 215654 | 3/1987 | European Pat. Off. . |
| 235085 | 9/1987 | European Pat. Off. . |
| 241147 | 10/1987 | European Pat. Off. . |
| 58-78594 | 5/1983 | Japan . |
| 2166436 | 5/1986 | United Kingdom . |
| 2167751 | 6/1986 | United Kingdom . |
| 2176182 | 12/1986 | United Kingdom . |
| 2170499 | 8/1988 | United Kingdom . |

OTHER PUBLICATIONS

Burg, R. W. et al., Antimicrob. Agents Chemother., 15, 361–367 (1979).
Chen et al., Abstr. Pap. Am. Chem. Soc., 186 Meet. MBTD 28 (1983).
Cheremisinoff, P. N. and Ouellette, R. P., Eds., *Biotechnology*, Technomic Publishing Co., pp. 14–15 (1985).
Daum, S. J. et al., Ann. Rev.Microbiol. 33, 241–265 (1979).
Fisher & Mrozik, *Macrolide Antibiotics*, Academic Press, Chapter 14 (1984).
Gray, P. P. et al., J. Ferm. Technol., 50, 381–387 (1971).
Martin et al., J. Bacteriology, 115, 198–204 (1973).
*Manual of Methods for General Microbiology*, P. Gerhardt, Editor–in–Chief, American Society for Microbiology, Washington, DC, pp. 365–370 (1981).
Ruby et al., 6th Intl. Symp. on Actinomycete Biology, pp. 279–280 (1985).
Ruby et al., 6th Intl. Symp. on "Biology of Actinomycetes," Debrecen, Hungary, Aug. 26–30 (1985).
Schulman et al., Antimicrobial Agents and Chemotherapy, 29, 620–624 (1986).
Schulman et al., Antimicrobial Agents and Chemotherapy, 31, 744–747 (1987).
Schulman et al., Fed. Proc., 44, 931 (1985).
Schulman et al., J. Antibiot., 38(11), 1494–1498 (1985).
Schulman, M. D. et al., J. Antibiotics, 34, 541–549 (1986).
Tabor et al., J. Bact., 128, 485–486 (1976).
Willecke et al., J. Biol. Chem., 246, 5264–5272 (1971).
Lehninger, A. L., *Short Course in Biochemistry*, Worth Publisher, Inc., New York, NY (1973).

*Primary Examiner*—Irene Marx
*Attorney, Agent, or Firm*—Peter C. Richardson; Gregg C. Benson

[57] ABSTRACT

*Streptomyces avermitilis* lacking branched-chain amino acid transaminase activity and/or branched-chain 2-oxo acid dehydrogenase activity, methods for preparation thereof, and use thereof to produce natural and non-natural avermectins useful as parasiticides.

28 Claims, 3 Drawing Sheets

PROCESS FOR PRODUCTION OF AVERMECTINS

CROSS REFERENCE TO RELATED APPLICATION

This application is a continuation of U.S. application Ser. No. 08/060,452, filed May 11, 1993, now abandoned, which is a division of U.S. application Ser. No. 66,912, filed Feb. 27, 1991, now U.S. Pat. No. 5,238,848 which is a continuation of U.S. application Ser. No. 107,825, filed Sep. 13, 1987, which is a continuation-in-part of U.S. application Ser. No. 006,512, filed Jan. 23, 1987, now abandoned.

BACKGROUND OF THE INVENTION

1. Field of the Invention

This invention relates to strains of *Streptomyces avermitilis* lacking branched-chain amino acid transaminase activity and/or branched-chain 2-oxo acid dehydrogenase activity, to methods for producing said *S. avermitilis* and to the use of *S. avermitilis* to produce natural and non-natural avermectins.

2. Description of the Prior Art

U.S. Pat. Nos. 4,310,519 and 4,429,042 describe the avermectins, a complex of related agents having potent antiparasitic activity, and their production by aerobic fermentation of strains of *Streptomyces avermitilis*; namely, *S. avermitilis* ATCC Nos. 31267, 31271 and 31272. The last two strains cited represent a frozen vial and a lyophilized tube, respectively of a culture obtained by ultraviolet irradiation of *S. avermitilis* ATCC 31267.

EP 214,731, published Mar. 18, 1987, the counterpart of U.S. patent application Ser. No. 886,867, filed Jul. 16, 1986, discloses a number of compounds (referred to herein as non-natural avermectins) related to the natural or known avermectins but having a novel substituent group at the 25-position, and a process for their preparation by fermentation of an avermectin producing organism in the presence of certain specified carboxylic acids, or derivatives or precursors thereof. The *S. avermitilis* organisms used to produce the said novel C-25 substituted avermectins are *S. avermitilis* ATCC 31267, 31271, 31272 and NCIB 12121. The latter organism, described in EP 214,731, is derived from *S. avermitilis* ATCC 31271. It gives improved yields of the novel C-25 substituted avermectins when it is cultured in a semi-defined medium. Each of ATCC 31267, 31271, 31272 and NCIB 12121 may also produce, in addition to the novel C-25 substituted derivative, varying amounts of the known, or natural, avermectins wherein the 25-substituent is isopropyl or (S)-sec-butyl (1-methylpropyl).

The carbon skeleton of the avermectins (depicted in formula (I) below) is derived from acetates and propionates and the C-25 substituent of natural avermectins from L-isoleucine (R=(S)-sec-butyl) or L-valine (R=isopropyl) [Fisher and Mrozik, "Macrolide Antibiotics", Academic Press (1984) Ch. 14].

By "known" or "natural" avermectins is meant those avermectins produced by *S. avermitilis* ATCC 31267, ATCC 31271 and ATCC 31272 wherein the 25-position substituent is either isopropyl or (S)-sec-butyl(1-methylpropyl). Avermectins wherein the 25-position substituent is other than isopropyl or sec-butyl (S-form) are referred to herein as novel or non-natural avermectins.

The strains of *S. avermitilis* cited in the above-mentioned U.S. patents produce a class of substances described generically therein as C-076. The class comprises eight distinct but closely related compounds described as C-076 A1a, A1b, A2a, A2b, B1a, B1b, B2a and B2b. The "a" series of compounds refers to the natural avermectins wherein the 25-substituent is (S)-sec-butyl and the "b" series to those wherein the 25-substituent is isopropyl. The designations "A" and "B" refer to avermectins wherein the 5-substituent is methoxy or hydroxy, respectively. Lastly, the numeral "1" refers to avermectins wherein a double bond is present at the 22-23 position; and numeral "2" to avermectins having a hydrogen at the 22-position and hydroxy at the 23 position.

In this application no such identifiers are used as regards the 25-substituent of the non-natural avermectins. Identifiers A1, A2, B1 and B2 have been retained to refer to non-natural avermectins having the structural features corresponding to those of the natural avermectins as noted above.

Generation of mutants devoid of branched-chain alpha-keto acid dehydrogenase activity has been reported for *Bacillus subtilis*, Willecke and Pardee, J. Biol. Chem. 246, 5264–72 (1971) and *Pseudomonas putida*, Martin et al., J. Bacteriology, 115 198–204 (1973), but not for Streptomyces.

*S. avermitilis* Agly-1, a mutant strain which produces virtually only avermectin aglycones A1a and A2a is reported by Schulman et al. J. Antibiot. 38(11), 1494–1498 (1985). Also reported is the fermentation of *S. avermitilis* Agly-1 in the presence of sinefungin which caused increased production of avermectin aglycone B components. Likewise, *S. avermitilis* O8, a high producing strain for avermectins, when fermented in the presence of sinefungin as inhibitor of O-methyl transferases, resulted in production of avermectins lacking O-methyl groups on the aglycone at C-5 and in the oleandrose disaccharide moiety.

U.S. Pat. No. 4,378,353 describes C-076 related compounds and their preparation by cultivation of MA-5218, a mutant strain of *S. avermitilis* ATCC 31272, obtained therefrom by ultraviolet irradiation. The mutant is identified as ATCC 31780. The C-076 related compounds produced by said mutant lack the C-076 furan ring. Additionally, in certain of the compounds reported, one or both of the oleandrose sugar moieties have been cleaved while in others the 5-position group was oxidized to a keto group.

Three classes of O-methyltransferase mutants of *S. avermitilis* that produce avermectins lacking O-methyl groups have been reported by Ruby et al., 6th International Symposium on the "Biology of Actinomycetes", Debrecen, Hungary, Aug. 26–30 (1985) and by Schulman et al, Antimicrobial Agents and Chemotherapy 31, 744–7 (1987). The first class produces primarily B avermectins due to their inability to methylate the C-5 hydroxyl of the macrocyclic lactone ring. The second class produces 3'-O, 3"-O-bis-demethylavermectins (avermectins lacking the O-methyl substituent at the 3 position of both oleandrose monosaccharide residues), and which are referred to as demethylavermectins. The third class is unable to methylate at any position.

Schulman et al., Fed. Proc. 44, 931 (1985) disclose increased production of B avermectins by fermenting *S. avermitilis* in the presence of substances such as sinefungin, S-adenosylethionine and S-adenosylhomocysteine which inhibit the methylation of the C-5 hydroxy group of the aglycone moiety by the enzyme avermectin B-O-methyltransferase. *Streptomyces avermitilis* mutants which lack O-methyltransferase activity and produce increased amounts of avermectin B components are also disclosed and referred to by Schulman et al. in Antimicrobial Agents and Chemotherapy 29, 620–624 (1986).

Mutagenesis of *S. avermitilis* produces mutants which lack branched-chain 2-oxo acid dehydrogenase activity or branched-chain amino-acid transaminase activity. Mutagenesis of the thus-produced singly blocked mutants produces mutants which lack both branched-chain 2-oxo acid dehydrogenase activity and branched-chain amino acid transaminase activity. The mutants no longer possess the ability to produce significant amounts of the natural avermectins in the absence of added compound RCOOH wherein R is isopropyl or (S)-sec-butyl, or of a compound convertible to RCOOH during the fermentation process. Surprisingly and unexpectedly, however, the mutants have been found to produce avermectins, natural and non-natural, when fermented in the presence of an added compound R—COOH wherein R is isopropyl or (S)-sec-butyl, or other group disclosed herein, or of a precursor to said RCOOH. It is even more surprising that the herein described mutants which lack only branched-chain 2-oxo acid dehydrogenase activity, and which are unable to degrade L-isoleucine or L-valine, are able to assimilate a wide variety of compounds into the avermectin biosynthetic pathway with production of non-natural avermectins free of the presence of natural avermectins.

At least as surprising is the finding that the herein described branched-chain amino acid transaminase deficient mutants, which are unable to degrade L-isoleucine, L-leucine or L-valine and require these three amino acids in order to grow, are also able to assimilate other compounds to produce non-natural avermectins free of the presence of natural avermectins.

The natural avermectins, as noted, are produced as a complex mixture of eight distinct but closely related compounds; formula (I), R=isopropyl and (S)-sec-butyl. While they have been recovered in substantially pure form (see U.S. Pat. No. 4,429,042), the methodology is, at best, laborious. The production of non-natural avermectins according to the process described in EP 214,731 may also produce some of the natural avermectins in varying amounts due to the presence of the branched-chain 2-oxo acid dehydrogenase and the amino acids L-valine and L-isoleucine in the cell of the *S. avermitilis* micro-organisms used in their production.

The ability to choose to produce either natural or non-natural avermectins so as to minimize the number and complexity of the products, and by so doing to increase the purity of a chosen avermectin, and thereby to simplify separation procedures, is a desirable goal.

SUMMARY OF THE INVENTION

*S. avermitilis* strains lacking branched-chain 2-oxo acid dehydrogenase activity or branched-chain amino acid transaminase activity are produced by mutation of avermectin producing strains of *S. avermitilis* and especially by mutation of *S. avermitilis* ATCC 31267, ATCC 31271, ATCC 31272 or NCIB 12121. Further mutation of either of said deficient strains produces strains deficient in both activities. The mutants are unable to synthesize the natural avermectins except where the fatty acid, or a precursor thereto, bearing the isopropyl or sec-butyl (S-form) group is added to the medium in which the mutants are fermented. They are capable of producing natural and non-natural avermectins when fermented under aqueous aerobic conditions in a nutrient medium containing an appropriate primer acid or compound convertible thereto in the fermentation process.

Those mutants characterized by their lack of branched-chain 2-oxo acid dehydrogenase activity, are isolated from the mutagenized colonies on the basis of a $^{14}CO_2$ assay. In this procedure the absence of $^{14}CO_2$ evolution by a permeabilized colony from a substrate of [$^{14}C$-1]-2-oxoisocaproic acid or [$^{14}C$-1]-2-oxo-3-methylvaleric acid or [$^{14}C$-1]-2-oxo-3-methylbutyric acid indicates absence of branched-chain 2-oxo acid dehydrogenase activity.

Those mutants characterized by their lack of amino acid transaminase activity are selected from the mutagenized colonies on the basis of their inability to grow on a medium which lacks L-isoleucine, L-leucine and L-valine. In practice, single colonies growing on an M9 salts glucose-based agar medium supplemented with all the individual amino acids found in casamino acid are transferred to a similar medium but which lacks L-isoleucine, L-leucine and L-valine. The herein described mutants which are deficient in only branched-chain amino acid transferase activity are able to use 2-oxo acids as precursors for production of avermectins.

It was surprising and unexpected that the herein-described mutants lacking branched-chain 2-oxo acid dehydrogenase activity and/or branched-chain amino acid transaminase activity retained the ability to produce avermectins, especially non-natural avermectins. The inability of the mutants to produce the natural fatty acyl coenzyme A derivatives when grown on a conventional medium could have been a lethal mutation if membrane integrity depended upon said derivatives or if 2-oxo acid accumulation by the former mutant led to cytotoxicity. Furthermore, neither of the mutants were expected to be able to synthesize acetyl CoA and propionyl CoA from L-isoleucine and L-valine degradative metabolism as this requires the enzyme activities that the mutants are missing. The requirement for these acyl CoA derivatives for avermectin biosynthesis, noted above, led to the expectation that the mutants might be severely impaired in non-natural avermectin production, which, surprisingly, was not the case.

The lack of branched-chain 2-oxo acid dehydrogenase activity in the mutants described herein results in the prevention of branched-chain fatty acyl CoA synthesis from the degradation of L-isoleucine, L-leucine and L-valine and, thereby, the synthesis of the natural avermectins. In like manner, the branched-chain amino acid transaminase-negative mutants of *S. avermitilis* also possess this characteristic lack of branched-chain fatty acyl CoA synthesis, and, therefore, the inability to produce the natural avermectins. This lack of fatty acyl CoA is due to two reasons. First, such transaminase-negative mutants are not able to synthesize branched-chain 2-oxo acids from medium-supplied isoleucine, leucine and valine via the normal route of transamination. Secondly, in these transaminase mutants, branched-chain 2-oxo acid production by the cellular branched-chain amino acid biosynthetic pathway is prevented by the necessary inclusion of these amino acids in the fermentation growth medium. The presence of these amino acids prevents operation of this biosynthetic pathway (and production of the intermediate 2-oxo acids) by well-known mechanisms of enzyme repression and feed-back inhibition by these amino acid end products of the pathway. The unavailability of these 2-oxo acids, which are substrates for the active branched-chain 2-oxo acid dehydrogenase enzyme, effectively prevents branched-chain fatty acyl CoA synthesis. Thus, the present invention encompasses the use of such 2-oxo acid dehydrogenase negative and transaminase-negative mutants, and mutants in which both the branched-chain transaminase negative and 2-oxo acid dehydrogenase-negative mutations are combined.

The present invention also includes any organism, regardless of its appearance or physiological behavior, that may be developed by means of transformation, transduction, genetic recombination or some other genetical procedure, using a nucleic acid or an equivalent material from the herein described species, whereby it has acquired the characteristics of the herein described mutants.

The terms "avermectin" or "avermectins" as used herein refers to compounds having formula (I) below but wherein the 25-substituent (R) can be any group assimilable at said position by the S. avermitilis of this invention.

The herein described mutants are highly valuable for producing non-natural avermectins by the processes disclosed and exemplified herein. They are especially valuable for production of preferred avermectins, i.e., compounds wherein the C-25 substituent is $C_4$–$C_6$ cycloalkyl or cycloalkenyl, optionally substituted by $C_1$–$C_4$ alkyl group; 1-methylthioethyl, or a 5- or 6-membered oxygen or sulfur heterocyclic group, especially 3-thienyl or 3-furyl.

DETAILED DESCRIPTION OF THE INVENTION

Mutation of an avermectin producing member of the species *Streptomyces avermitilis* is carried out according to known procedures using any of a variety of mutating agents including ultraviolet irradiation, X-ray irradiation, N-methyl-N'-nitro-N-nitrosoguanidine, ethylmethane sulfonate, nitrous acid and nitrogen mustards, e.g., N-methylbis(2-chloroethyl)amine, or like treatments. The mutagenesis can be conducted on spores or on a vegetative culture of *S. avermitilis* capable of producing natural avermectins, e.g., *S. avermitilis* ATCC 31272.

Following procedures well known to those skilled in the art, mutagenized colonies are selected for lack of branched-chain 2-oxo acid dehydrogenase on the basis of a biochemical assay method which permits screening of large numbers of randomly mutagenized bacterial colonies for $^{14}CO_2$ production from [$^{14}C$-1]-2-oxo acids (Tabor et al., J. Bact. 128, 485–486, 1976).

The methodology comprises growing the mutant colonies in the wells of a microtiter plate on a suitable nutrient medium, permeabilizing the cells with toluene followed by adding the [$^{14}C$-1]-2-oxo acid (e.g. 2-oxoisocaproic acid) to each well and checking the atmosphere above the fermentation for $^{14}CO_2$. Alternatively, [$^{14}C$-1]-2-oxo-3-methylvaleric acid, or [$^{14}C$-1]-2-oxo-3-methylbutyric acid can be used in place of [14C-1]-2-oxo-isocaproic acid Production of $^{14}CO_2$ is conveniently checked for by placing moist Ba(OH)$_2$-saturated filter paper above the individual wells to trap any $^{14}CO_2$ released and detection of Ba$^{14}CO_3$, if any, by autoradiography. Mutants which lack branched-chain 2-oxo acid dehydrogenase activity give autoradiograms approximating those of blank controls; i.e., no Ba$^{14}CO_3$ is produced by the mutants.

The mutants thus obtained are subjected to further mutagenesis using any of the above-mentioned mutating agents. Mutagenesized colonies are selected for lack of branched-chain amino acid transaminase activity on the basis of their failure to grow on M9/glucose minimal plates except in the presence of L-isoleucine, L-leucine and L-valine (ILV). All three amino acids must be present for growth to occur. Further, it has been demonstrated that said transaminase negative mutants do not grow on media supplemented with all three of the keto acids which serve as substrates for the transaminase reactions. A single transaminase enzyme thus catalyzes transamination of each of the three keto acids (2-oxo-3-methyl valeric acid, 2-oxo-isocaproic acid, 2-oxo-isovaleric acid).

The doubly blocked mutants, those lacking both branched-chain 2-oxo acid dehydrogenase and branched-chain amino acid transaminase, activities are of particular interest since the probability of their reverting to cultures which produce the natural avermectins is extremely low. The singly blocked mutants may, under certain circumstances, revert to cultures which would produce natural avermectins.

In addition to production of desired alleles of a given strain of microorganism by mutagenesis, protoplast fusion permits introduction of desirable alleles produced/identified in one strain into the chromosome of another strain. For example, a strain of *S. avermitilis* deficient in branched-chain 2-oxo acid dehydrogenase activity and branched-chain amino acid transaminase activity can, by protoplast fusion with a *S. avermitilis* strain having the aforementioned activities produce a strain of *S. avermitilis* deficient only in branched-chain amino acid transaminase activity. As those skilled in the art recognize, protoplast fusion technology enables combination of desirable alleles from divergent lines of selection into a single strain. The herein described *S. avermitilis* JC-923 (ATCC 53669), a branched-chain amino acid transaminase deficient strain was produced via this technology.

The morphological and cultural characteristics of the mutants of this invention are generally as described in U.S. Pat. No. 4,429,042. The distinguishing characteristic of the mutants of this invention is their lack of branched-chain 2-oxo acid dehydrogenase activity and/or of branched-chain amino acid transaminase activity which characteristics are determined as described herein. The lack of said activities results in the failure of the mutants to produce the natural avermectins when grown on a defined medium substantially free of fatty acids RCOOH wherein R is isopropyl or (S)-sec-butyl, or compounds convertible to said RCOOH during fermentation. A taxonomic investigation conducted by the American Type Culture Collection, confirmed that the characteristics of two mutant strains I-3 and HL-026, selected by the above $^{14}CO_2$ assay, bear a close relationship to those of the parental ATCC 31272 strain described in U.S. Pat. No. 4,429,042, but with certain exceptions. Thus, mutant strain I-3 (ATCC 53567) forms significantly fewer spore chains than does ATCC 31272, and mutant strain HL-026 (ATCC 53568) is practically devoid of aerial mycelia and spores, but the very few spore chains it produces are of similar character to those of ATCC 31272. Also, mutant HL-026 exhibits a doubtful capacity to utilize raffinose as a sole carbon source, whereas the ATCC 31272 strain and mutant I-3 strain are able to use raffinose. (In experiments by applicants, raffinose did not appear to support the growth of any of these strains). One further characteristic of mutant strain HL-026 was that it produced less melanin pigment than the other two strains and uniquely none at all on tyrosine agar. Finally, in contrast to the description given for ATCC 31272 in U.S. Pat. No. 4,429,042, we are unable to detect growth of the mutants or of ATCC 31272 with sucrose as sole carbon source. Mutants I-3 and HL-026 are deficient only in branched-chain 2-oxo acid dehydrogenase activity. The doubly deficient mutant PGS-119 (ATCC 53670), produced by further mutagenesis of mutant I-3 (ATCC 53567), and JC-923 (ATCC 53669), obtained by protoplast fusion, bears a similar taxonomic relation to ATCC 31272 as does mutant strain I-3.

*Streptomyces avermitilis* I-3, HL-026, PGS-119 and JC-923 have been deposited under the terms of the Budapest Treaty in the American Type Culture Collection, Rockville, Md., a recognized depository affording permanence of the deposits and ready accessibility thereto by the public if a patent is granted on this application. They have been given the designation *Streptomyces avermitilis* ATCC 53567, ATCC 53568, ATCC 53670 and ATCC 53669, respectively. The deposits are available during pendency of this application to one determined by the Commissioner of the United States Patent and Trademark Office to be entitled thereto under 37 CFR 1.14 and 35 USC 122, and in accordance with foreign patent laws in countries wherein counterparts of this application, or its progeny, are filed. All restrictions on the availability to the public of the microorganisms deposited will be irrevocably removed upon granting of the patent.

Each of *S. avermitilis* ATCC 31267, ATCC 31271, ATCC 31272 and NCIB 12121 produces the natural avermectins, formula (I) compounds

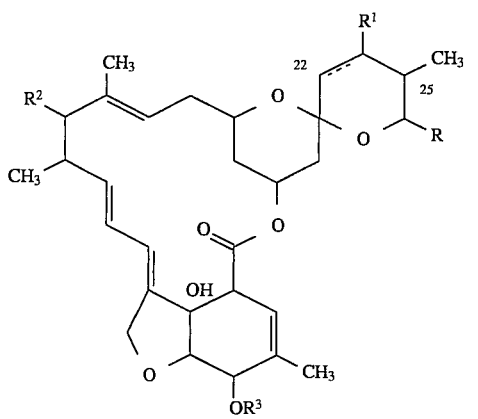

wherein the broken line at the 22-23 position represents an optional double bond;

$R^1$ is hydroxy and is present only when the double bond is absent;

$R^2$ is 4'-(alpha-L-oleandrosyl)-alpha-L-oleandrosyloxy of the formula

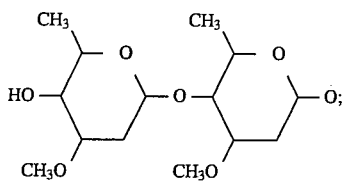

$R^3$ is hydrogen or methyl; and

R is isopropyl or (S)-sec-butyl. U.S. Pat. No. 4,285,963 describes an avermectin of formula (I) wherein the 25-position is substituted with a methyl and an ethyl group; $R^1$ is hydroxy and $R^3$ is methyl.

In the non-natural avermectins referred to herein R is a substituent other than isopropyl or (S)-sec-butyl and is as defined below.

The compounds essential for utilization in the biosynthesis of formula (I) compounds occur in the cell of *S. avermitilis*. These compounds, L-valine, L-leucine and L-isoleucine, are believed to enter into the biosynthesis of avermectins via conversion to 2-oxo acid and decarboxylation of the acid by branched-chain 2-oxo acid dehydrogenase, concomitant with coupling the product with coenzyme A. Their presence accounts for the concurrent production of both the isopropyl and (S)-sec-butyl compounds of formula (I). This, of course, gives rise to problems in separating the isopropyl from the (S)-sec-butyl derivatives.

When fermented in a nutrient medium containing the appropriate primer compound the mutants of this invention produce a compound of formula (I) or, as is more usually the case, a mixture of two or more compounds of formula (I) in which R corresponds to the primer compound used. Up to four products, conveniently and trivially referred to as R-avermectin A1, A2, B1 and B2, according to the designations used in U.S. Pat. No. 4,429,042, can be produced. The "R-" group, of course, refers to the C-25 substituent. For example, when R is cyclopentyl the four possible avermectins are:

| Trivial Name | $R^1$ | $R^3$ |
|---|---|---|
| cyclopentyl avermectin A1 | double bond | $CH_3$ |
| cyclopentyl avermectin A2 | hydroxy | $CH_3$ |
| cyclopentyl avermectin B1 | double bond | H |
| cyclopentyl avermectin B2 | hydroxy | H |

In the non-natural avermectins the C-25 substituent "R" of formula (I) is other than isopropyl or (S)-sec-butyl.

Compounds of formula (I) wherein the double bond is present and OH is absent may alternatively be prepared from the corresponding compound of formula (I) wherein $R^1$ is OH and the double bond is absent by a dehydration reaction. The reaction is performed by first selectively protecting the hydroxy groups at the 5 and 4" positions, e.g. as the t-butyldimethylsilyloxy acetyl derivative, then reacting with a substituted thiocarbonyl halide, such as (4-methylphenoxy)thiocarbonyl chloride, followed by heating in a high boiling point solvent, e.g. trichlorobenzene, to effect the dehydration. The product is finally deprotected to give the unsaturated compound. These steps together with appropriate reagents and reaction conditions are described in U.S. Pat. No. 4,328,335.

Formula (I) compounds wherein $R^3$ is H may also be prepared from the corresponding compounds wherein $R^3$ is $CH_3$ by demethylation. This reaction is achieved by treating the 5-methoxy compound, or a suitably protected derivative thereof, with mercuric acetate and hydrolyzing the resulting 3-acetoxy enol ether with dilute acid to give the 5-keto compound. This is then reduced using, for example, sodium borohydride to yield the 5-hydroxy derivative. Appropriate reagents and reaction conditions for these steps are described in U.S. Pat. No. 4,423,209.

Compounds of formula (I) wherein $R^1$ is H and the double bond is absent can be prepared from the corresponding compound wherein the double bond is present and $R^1$ is absent, by selective catalytic hydrogenation using an appropriate catalyst. For example, the reduction may be achieved using tris(triphenylphosphine)rhodium (I) chloride as described in European Patent Application Publication No. 0001689, and its counterpart U.S. Pat. No. 4,199,569, issued Apr. 22, 1980.

The compounds of formula (I) wherein $R^2$ is H are prepared from the corresponding compounds wherein $R^2$ is 4'-(alpha-L-oleandrosyl)-alpha-L-oleandrosyloxy by removing the 4'-(alpha-L-oleandrosyl)-alpha-L-oleandrose group by mild hydrolysis with an acid in an aqueous organic solvent to yield the aglycone having a hydroxy group at the 13-position; this is then halogenated, for example by reaction with a benzene sulfonyl halide, to yield the 13-deoxy-13-halo derivative which is finally selectively reduced, for example using tributyltin hydride. In order to avoid unwanted side reactions it is desirable to protect any other hydroxy groups which may be present, for example using a tert-butyldimethylsilyl group. This is then readily removed after the halogenation or reduction step by treatment with methanol containing a trace of acid. All these steps together with appropriate reagents and reaction conditions for their performance are described in European Patent Application Publication No. 0002615.

The compounds capable of utilization by the *S. avermitilis* of this invention for the biosynthesis of avermectins, natural and non-natural, are compounds of formula (II-A)

$$R—COOH \qquad (II\text{-}A),$$

including compounds convertible to (II-A) during the fermentation process. Said compounds are referred to herein as "primer compounds". In formula (II-A), R is an alpha-branched-chain group, the carbon atom thereof to which is attached the —COOH group is also attached to at least two other atoms or groups other than hydrogen. This definition, of course, embraces saturated and unsaturated acyclic and cyclic groups, including those optionally bearing a sulfur or oxygen heteroatom as a member of the acyclic chain or cyclic ring.

More specifically, R, which becomes the C-25 substituent, can be an alpha-branched $C_3$–$C_8$ alkyl, alkenyl, alkynyl, alkoxyalkyl or alkylthioalkyl group; a $C_5$–$C_8$ cycloalkylalkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms (fluoro, chloro, iodo or bromo); or a 3 to 6 membered oxygen or sulfur containing heterocyclic ring which may be saturated, or fully or partially unsaturated and which may optionally be substituted by one or more $C_1$–$C_4$ alkyl groups or halo atoms.

Compounds convertible to RCOOH; i.e., precursors, in the fermentation process are compounds of formulae (II-B) wherein R is as defined above:

$$R—(CH_2)_n—Z \qquad (II\text{-}B)$$

n is 0, 2, 4 or 6; and Z is —$CH_2OH$, —CHO, —$CH_2NH_2$, —$COOR^5$ or —$CONHR^6$ wherein $R^5$ is H or $(C_{1-6})$alkyl; $R^6$ is hydrogen, $(C_{1-4})$alkyl, or the residue of an amino acid, especially of aspartic acid, glutamic acid and methionine, e.g., —$CH(COOH)CH_2COOH$, —$CH(COOH)(CH_2)_2COOH$ and —$CH(COOH)(CH_2)_2SCH_3$, respectively.

In the case of *S. avermitilis* strains deficient only in branched-chain amino acid transaminase, 2-oxo acids also serve as precursors. Thus, for said strains acids of the formula (II-C)

$$R—CO—Z \qquad (II\text{-}C)$$

wherein R and Z are as defined above are capable of utilization by said *S. avermitilis* for the biosynthesis of avermectins.

Also included in this invention are the isomeric forms of formula (II-A) compounds, and compounds convertible thereto during the fermentation process, and the isomeric avermectins at C-25 resulting from their use in the herein described process.

The process of this invention is carried out by aerobically fermenting with a strain of *S. avermitilis* which lacks branched-chain 2-oxo acid dehydrogenase activity and/or branched-chain amino acid transaminase activity in an aqueous nutrient medium comprising an assimilable source of nitrogen, carbon, inorganic salts and a compound of formula RCOOH, or a compound convertible to said compound (i.e., a precursor) during the fermentation. The acid, or compound convertible thereto, is added to the fermentation either at the time of inoculation or at intervals during the fermentation. When a transaminase negative mutant is used, the medium must contain L-isoleucine, L-leucine and L-valine in order for growth of the mutant to occur. Production of the avermectin products may be monitored by removing samples from the fermentation, extracting with an organic solvent and following the appearance of the product by chromatography, for example, using high performance liquid chromatography. Incubation is continued until the yield of the product has been maximized, generally for a period of from 4 to 15 days.

A preferred level of each addition of the primer compounds (carboxylic acid or compound convertible thereto) is between 0.05 and 3.0 grams per liter. The primer compound can be added continuously, intermittently or all at once to the fermentation. The acid (RCOOH) is added as such or as a salt, such as the sodium, lithium or ammonium salt, or as a compound convertible to the acid as defined above. The acid, if a solid, is preferably dissolved in a suitable solvent such as water or $(C_{1-4})$alcohols.

The media used for the fermentation can, especially when the C-25 substituent is to be isopropyl or (S)-sec-butyl, be conventional media containing assimilable sources of carbon, nitrogen and trace elements. When the C-25 substituent is to be a non-natural group; i.e., it is not isopropyl or (S)-sec-butyl, the fermentation medium is one in which the chosen ingredients lack, or contain only minimal amounts of primer compounds wherein the R moiety is isopropyl or (S)-sec-butyl.

After fermentation for a period of several days at a temperature preferably in the range of 24° to 33° C., the fermentation broth is centrifuged or filtered and the mycelial cake is extracted with preferably acetone or methanol. The solvent extract is concentrated and the desired product is then extracted into a water-immiscible organic solvent, such as methylene chloride, ethyl acetate, chloroform, butanol or methyl isobutyl ketone. The solvent extract is concentrated and the crude product is further purified as necessary by chromatography, for example using preparative reverse phase, high performance liquid chromatography.

The product is generally obtained as a mixture of the compounds of formula (I) wherein $R^2$ is 4'-(alpha-L-oleandrosyl)-alpha-L-oleandrosyloxy, $R^1$ is OH and the double bond absent or $R^1$ is absent and the double bond is present and wherein $R^3$ is H or $CH_3$; however, the proportions can vary depending on the particular mutant and primer compound employed and the conditions used.

The source of the R group; i.e., whether it comes directly from R—COOH or is produced from one of the above precursors, or from any precursor, is immaterial to the production of the avermectins. The critical requirement of the process of this invention for their production is that the desired R group be made available to the *S. avermitilis* strains of this invention in the fermentation process.

Suitable compounds include the following:
2,3-dimethylbutyric acid
2-methylhexanoic acid
2-methylpent-4-enoic acid
2-cyclopropyl propionic acid
4,4-difluorocyclohexane carboxylic acid Lithium salt
4-methylenecyclohexane carboxylic acid
3-methylcyclohexane carboxylic acid (cis/trans)
1-cyclopentene carboxylic acid
1-cyclohexene carboxylic acid tetrahydropyran-4-carboxylic acid
thiophene-2-carboxylic acid
3-furoic acid
2-chlorothiophene-4-carboxylic acid
cyclobutane carboxylic acid
cyclopentane carboxylic acid
cyclohexane carboxylic acid
cycloheptane carboxylic acid
2-methylcyclopropane carboxylic acid
3-cyclohexene-1-carboxylic acid
2-methylthiopropionic acid
2-methyl-4-methoxybutyric acid
thiophene-3-carboxylic acid
hydroxymethylcyclopentane
3-thiophene carboxaldehyde
3-cyclohexylpropionic acid
3-cyclopentylpropionic acid
hydroxymethylcyclobutane
tetrahydrothiophene-3-carboxylic acid
3-cyclopentyl-1-propanol
3-methylcyclobutane carboxylic acid Lithium salt
3-fluorocyclobutane carboxylic acid
3-methylenecyclobutane carboxylic acid Lithium salt
2-methyl-4-methylthiobutyric acid
tetrahydrothiopyran-4-carboxylic acid
cyclobutylmethylamine
ethyl cyclobutanecarboxylate
4-hydroxymethylcyclopentene
2-(3-thiophenecarbonyl)propionic acid ethyl ester
(S)-2-methylpentanoic acid
(R)-2-methylpentanoic acid O-methyltransferase mutants can be obtained from the herein-described branched-chain 2-oxo acid dehydrogenase negative mutants and/or branched-chain amino acid transaminase negative mutants. Mutants in which a mutation in active branched-chain 2-oxo acid dehydrogenase activity and/or branched-chain amino acid transaminase activity is combined with one or both of the O-methyltransferase mutations yield strains of S. avermitilis that will, when fed RCOOH compounds or compounds convertible to RCOOH during the fermentation process, produce primarily B avermectins, demethylavermectins or demethylavermectin B compounds. Said mutants are obtained by mutagenesis of the herein described mutants which lack branched-chain 2-oxo acid dehydrogenase activity and/or branched-chain amino acid transaminase activity by means of ultraviolet light and/or chemical mutagens such as N-methyl-N-nitrosourethan, nitrosoguanidine, ethyl methane sulfonate or other agent such as those enumerated above. Alternatively, branched-chain 2-oxo acid dehydrogenase positive mutants and/or branched-chain amino acid transaminase positive mutants which lack one or both of the O-methyltransferases can be mutated by treatment with UV light or a mutagenizing agent to produce the branched-chain 2-oxo acid dehydrogenase negative mutants and/or branched-chain amino acid transaminase negative mutants.

The non-natural avermectins produced by such mutants are characterized by the presence of hydroxy groups at the C-5 position of the aglycone moiety and/or the C-3' and/or C-3" positions of the oleandrose moieties.

The above-described mutants are identified according to the methodology described by Schulman et al. Antimicrobial Agents and Chemotherapy, 29,620–624 (1986). They are useful for the same purposes and in the same way as are the known avermectins.

Alternatively, increased amounts of the B avermectins, including those lacking methyl groups on the oleandrose disaccharide moiety, are produced by fermenting the mutants of this invention, which lack active branched-chain 2-oxo acid dehydrogenase and/or branched-chain amino acid transaminase activity, in the presence of a substance such as sinefungin, S-adenosylethionine or S-adenosylhomocysteine which inhibits O-methyl transferase activity.

The compounds of the invention are highly active antiparasitic agents having particular utility as anthelmintics, ectoparasiticides, insecticides and acaricides.

Thus the compounds are effective in treating a variety of conditions caused by endoparasites including, in particular, helminthiasis which is most frequently caused by a group of parasitic worms described as nematodes and which can cause severe economic losses in swine, sheep, horses and cattle as well as affecting domestic animals and poultry. The compounds are also effective against other nematodes which affect various species of animals including, for example, Dirofilaria in dogs and various parasites which can infect humans including gastro-intestinal parasites such as Ancylostoma, Necator, Ascaris, Strongyloides, Trinchinella, Capillaria, Trichuris, Enterobius and parasites which are found in the blood or other tissues and organs such as filiarial worms and the extract intestinal states of Strongyloides and Trichinella.

The compounds are also of value in treating ectoparasite infections including in particular arthropod ectoparasites of animals and birds such as ticks, mites, lice, fleas, blowfly, biting insects and migrating dipterous larvae which can affect cattle and horses.

The compounds are also insecticides active against household pests such as the cockroach, clothes moth, carpet beetle and the housefly as well as being useful against insect pests of stored grain and of agricultural plants such as spider mites, aphids, caterpillars and against migratory orthopterans such as locusts.

The compounds of formula (I) are administered as a formulation appropriate to the specific use envisaged and to the particular species of host animal being treated and the parasite or insect involved. For use as an anthelmintic the compounds may be administered orally in the form of a capsule, bolus, tablet or a liquid drench, or alternatively, they may be administered by injection or as an implant. Such formulations are prepared in a conventional manner in accordance with standard veterinary practice. Thus capsules, boluses or tablets may be prepared by mixing the active ingredient with a suitable finely divided diluent or carrier additionally containing a disintegrating agent and/or binder such as starch, lactose, talc, magnesium stearate etc. A drench formulation may be prepared by dispersing the active ingredient in an aqueous solution together with dispersing or wetting agents, etc., and injectable formulations may be prepared in the form of a sterile solution which may contain other substances, for example, enough salts or glucose to make the solution isotonic with blood. These formulations will vary with regard to the weight of active compound depending on the species of host animal to be treated, the severity and type of infection and the body weight of the host. Generally for oral administration a dose of from about 0.001 to 10 mg per kg of animal body weight given as a single dose or in divided doses for a period of from 1 to 5 days will be satisfactory, but, of course, there can be instances where higher or lower dosage ranges are indicated and such are within the scope of this invention.

As an alternative the compounds may be administered with the animal feedstuff and for this purpose a concentrated feed additive or premix may be prepared for mixing with the normal animal feed.

For use as an insecticide and for treating agricultural pests the compounds are applied as sprays, dusts, emulsions and the like in accordance with standard agricultural practice.

Production of Branched-chain 2-oxo Acid

Dehydrogenase Deficient *S. avermitilis* I-3 (ATCC 53567)
Step 1

*S. avermitilis* ATCC 31272 was grown as a confluent lawn on New Patch Agar Medium for 12 days at 30° C. The medium comprised

| V-8 Juice* | 200 ml |
|---|---|
| $CaCO_3$ | 3 grams |
| Agar | 15 grams |
| $H_2O$ to | 1000 ml |
| Nutrient broth | 1.0 grams/L |
| sodium acetate.$3H_2O$ | 1.4 grams/L |
| isovaleric acid | 50 mg/L |
| isobutyric acid | 50 mg/L |
| 2-methylbutyric acid | 50 mg/L |
| isoleucine | 250 mg/L |
| leucine | 250 mg/L |
| valine | 250 mg/L |
| trace elements solution** | 1 ml/L |

*A mixture of 8 vegetable juices (tomato, carrots, celery, beets, parsley, lettuce, watercress and spinach) plus salt, ascorbic and citric acids and natural flavors. Available from Campbell Soup Company, Camden, NJ.
**Composition of Trace elements solution:

| $FeCl_3.6H_2O$ | 2.7 g |
|---|---|
| $MnSO_4.H_2O$ | 4.2 |
| $CuSO_4.5H_2O$ | 0.5 |
| $CaCl_2$ | 11.0 |
| $H_3BO_3$ | 0.62 |
| $CoCl_2.6H_2O$ | 0.24 |
| $ZnCl_2$ | 0.68 |
| $Na_2MoO_4$ | 0.24 |

Dissolve the above in 1 liter of 0.1N HCl.

Spores were harvested from 3 such plates and suspended in 20 ml. of 0.05M tris-maleic acid buffer, pH 9.0.
Step 2.

10 ml of the spore suspension was added to a vial containing 10 mg of N-methyl-N'-nitro-N-nitrosoguanidine (NTG). The vial was incubated and shaken at 28° C. for 60 minutes and the spores then washed profusely with 1% NaCl solution.
Step 3.

The washed spores were suspended in 1% NaCl and mixed with an equal volume of 80% ethylene glycol. This suspension was preserved at −20° C. and used as a source of cells to be screened for mutants. It gave approximately $10^4$ colonies/ml when germinated.

This spore stock was spread on YPD plates to yield approximately 100 colonies per plate (YPD medium comprises 10 g/l of each of yeast extract, Bacto peptone* and dextrose; and 15 g/l of Bacto agar*, adjusted to pH 6.9 before autoclaving) Ingredients marked with an asterisk are available from Difco Laboratories, Detroit, Mich. 48238.
Step 4.

Single colonies were picked from plates after 2–3 weeks of growth at 28° C. and placed in individual wells of a standard 96 well microtiter plate. Also, a small quantity of the colony was patched onto a fresh agar medium to serve as a source of viable cells when mutants are identified.
Step 5.

To each well was added approximately 75 microliters of a liquid M9 salts medium containing 1% glucose, 0.1% casamino acids, and 0.01% of each of isovaleric, isobutyric and 2-methylbutyric acids. After several days of incubation at 28° C., the cells were assayed for the presence of branched-chain 2-oxo acid dehydrogenase. (Each liter of M9 salts medium comprises 6 g $Na_2HPO_4$, 3 g $KH_2PO_4$, 0.5 g NaCl and 1 g of $NH_4Cl$. The medium is autoclaved and then 1 ml of each of sterilized 1M $MgSO_4$ and 0.1M $CaCl_2$ are added aseptically).
Step 6.

A microsuspension of 5% toluene in M9 salts medium was prepared by a brief sonication of the immiscible mixture. To 25 ml of this suspension was added 1.2 ml of a solution containing [$^{14}C$-1]-2-oxo-isocaproic acid, 2.5 microcurie/ml and 10.0 microcurie/micromole. 50 Microliters of this overall mixture was added to each of the wells of the microtiter plates containing the colonies to be assayed.
Step 7.

The $^{14}CO_2$ produced from each well was trapped and visualized by the procedure described by Tabor et al., *J. Bacteriol.* 128 485–486 (1976) entitled "Convenient Method for Detecting $^{14}CO_2$ in Multiple Samples: Application to Rapid Screening for Mutants". Mutants lacking active branched-chain 2-oxo acid dehydrogenase produce no $Ba^{14}CO_3$ beyond that observed for the controls.

A more refined method which improves the contrast between a positive assay for $^{14}CO_2$, indicated by a dark spot on the autoradiogram as a result of $Ba^{14}CO_3$ formation, and a negative assay indicated by no spot or a very light spot, comprises the following modified screen.

Single colonies (see Step 4 above) were picked from the agar medium after 7–14 days of growth (rather than 2–3 weeks and assayed directly by steps 6 and 7 above). Step 5 of the above procedure is omitted.

An even more refined assay method which is quantitative in nature as regards $^{14}CO_2$ release comprises growing the mutants detected by the above screens on a suitable medium comprising M9 salts medium with glucose, 1% and "Syncasa-bcaa", 0.1% (a synthetic mixture of L-amino acids with the approximate composition of commercial casamino acids, but without the presence of L-valine, L-isoleucine and L-leucine, see below).

After growth to high cell density, the cells were washed in M9 salts medium and resuspended in cold M9 salts medium containing 1% toluene which had been sonicated to produce a milky white dispersion of the toluene. The cell/buffer/toluene suspension was incubated for 40 minutes at 30° C. in order to permeabilize the cells. The permeabilized cells were then washed in M9 medium salts and finally resuspended in one-fifth the original volume of M9 medium buffer. 180 Microliters of this suspension were used per assay.

A reaction volume of 300 microliters contained the toluenized cells, thiamine pyrophosphate (TPP), 0.4 mM; coenzyme A (CoA), 0.11 mM; nicotinamide adenine dinucleotide (NAD), 0.68 mM, dithiothreitol (DTT), 2.6 mM; $MgCl_2$, 4.1 mM; Tris-HCl, 60 mM; Tris-HCl, 60 mM, pH 7.5; and [$^{14}C$-1]-alpha-ketoisocaproate, 6,000 cpm, microcurie per micromole. The efficiency of counting was 73%. The reaction was carried out in 15 ml scintillation vials containing a 2×2 cm Whatman #4 paper square pressed into the screw cap of the vial. The paper contains 30 microliters of 1M Hyamine Hydroxide (1M solution of methylbenzethonium hydroxide in methanol; available from Sigma Chemical Co., St. Louis, Mo. 63178), which traps $^{14}CO_2$ evolved in the reaction. After incubation for 2 hours, the papers are immersed in 10 ml of Beckman Aquasol II (Universal LSC (liquid scintillation counter) available from New England Nuclear Research Products, Boston, Mass. 02118) and the radioactivity measured in a liquid scintillation counter after equilibration in this solvent for 4 hours or more. A blank control reaction (i.e.—no cells) gives ca. 50–300 cpm.

Mutant I-3 and others like it gave counts that were less than or equal to the blank control reaction, whereas the parent strain gave counts several fold higher than the blank control value.

Isolation of HL-026 Derivative (ATCC 53568) of S. Avermitilis I-3 (ATCC 53567)

S. avermitilis I-3 (ATCC 53567) was streaked out on nutrient agar plates. A relatively high frequency of spontaneous variants appeared, some of which lacked aerial mycelium upon 4 days incubation at 30° C. Several of such variants were isolated and tested for their ability to produce non-natural avermectins when fermented in AP-5 medium to which cyclopentane carboxylic acid was added. From the isolates, many of which produced non-natural avermectins free of natural avermectins, a strain which yielded higher titers of avermectins in flask experiments than its parent S. avermitilis I-3 (ATCC 53567) was assigned identification number HL-026 (ATCC 53568).

Production of Branched-chain 2-oxo Acid Dehydrogenase Deficient and Branched-chain Amino Acid Transaminase Deficient S. avermitilis PGS-119 (ATCC 53670)

Step 1.
Approximately 100 mg of S. avermitilis I-3 (ATCC 53567), grown on a fresh SAMM agar plate for four days, was inoculated into a 300 ml flask containing 50 ml of SCM medium (pH 7.2). The flask was then shaken at 200 RPM and 30° C. for twenty-four hours (final pH=8.2).
Step 2.
The flask was removed from the shaker and 10 ml of the whole broth centrifuge$_d$ in a sterile tube for five minutes at 2000 RPM. The cells were then resuspended in 50 ml of SCM medium in sterile 300 ml. Erlenmeyer flasks and the flasks shaken on a rotary shaker for two hours at 30° C.
Step 3.
The 10 ml of the suspension was placed in a sterile tube.
Step 4.
Ethylmethane sulfonate (250 μl) was added to the tube (in a well ventilated hood), the contents thoroughly mixed, then poured into a sterile 300 ml flask and the flask shaken in a rotary shaker for three hours at 30° C.
Step 5.
Fresh sterile SCM medium (40 ml) was added to the flask and shaking continued for a total of 70 hours at 30° C.
Step 6.
The flask was removed, the contents spun down at 8000 RPM for ten minutes at 20° C. The cells were washed by re-suspending in SCM medium, spun down again and re-suspended in 10 ml SCM medium.
Step 7.
Cells were removed and assayed via replica plating, ca. 150 colonies/plate, for their ability to grow on M9/glucose minimal plates in the presence and absence of L-leucine, L-isoleucine, L-valine and combination of any of said amino acids. The mutant cells of interest grew only on media supplemented with L-leucine, L-isoleucine and L-valine. These derivatives of S. avermitilis I-3 (ATCC 53567), deficient in branched-chain amino acid transaminase activity, also failed to grow on media supplemented with one or more of the three 2-oxo acids (2-oxoisocaproic acid; 2-oxo-3-methylvaleric acid and 2-oxoisovaleric acid) which serve as precursors for L-leucine, L-isoleucine and L-valine. This behavior is completely opposite to that of S. avermitilis I-3 (ATCC 53567) which grew well on such media. Thus, a single transaminase enzyme catalyzes transamination of said 2-oxo acids.

| SCM MEDIUM | |
|---|---|
| Yeast autolysate | 10 g/l |
| Beef extract | 5 g/l |
| Casein enzymatic hydrolysate | 10 g/l |
| 1M MgSO$_4$ | 3 g/l |
| 1M K$_2$HPO$_4$; pH 7.0 (HCl) | 100 g/l |

| SAMM Agar Plate | |
|---|---|
| | g/L |
| Na$_2$HPO$_4$ | 6.0 |
| KH$_2$PO$_4$ | 3.0 |
| NaCl | 0.5 |
| NH$_4$Cl | 1.0 |
| 1M MgSO$_4$ | 1.0 |
| 0.1M CaCl$_2$ | 1.0 |
| Dextrose | 8.0 |
| Casamino Acids | 20.0 |
| Agar | 20.0 |

| Composition of "Syncasa - bcaa", 100 fold Concentrate | |
|---|---|
| | grams/liter |
| L-alanine | 3 |
| L-arginine | 4 |
| L-aspartic acid | 6 |
| L-cystine | 1 |
| L-glutamic acid | 20 |
| glycine | 1 |
| L-histidine | 2 |
| L-lysine | 7 |
| L-methionine | 3 |
| L-phenylalanine | 6 |
| L-proline | 10 |
| L-serine | 6 |
| L-threonine | 4 |
| L-tyrosine | 4 |
| L-tryptophan | 1 |

The mixture is adjusted to pH 7 and filter sterilized.
One volume of concentrate is added to 99 volumes of medium to achieve standard use concentrations.
S. avermitilis JC-923 (ATCC 53669) by Protoplast Fusion of a Spectinomycin Resistant Strain of S. avermitilis ATCC 31272 and S. avermitilis PGS 119 (ATCC 53670).

S. avermitilis ATCC 31272 spectinomycin resistant, is a spontaneous mutant of S. avermitilis ATCC 31272. It was isolated from populations of vegetative mycelia of ATCC 31272 spread on AS-1 agar plates containing 50 mcg/ml of spectinomycin. Spores of the mutant germinated on rich medium are resistant to 50 mcg/ml spectinomycin, as compared to spores of the isogenic parental strain which fail to germinate under these conditions. This dominant selectable marker was used successfully to isolate branched-chain amino acid transaminase-deficient isolates of ATCC 31272.

| AS-1 agar (Rich plating medium for Streptomyces) | |
|---|---|
| Yeast extract | 1 g |
| L-Alanine | 0.2 g |
| L-Arginine | 0.2 g |
| L-Asparagine | 0.5 g |
| Soluble starch | 5 g |
| NaCl | 25 g |
| Na$_2$SO$_4$ | 10 g |

| AS-1 agar | |
| --- | --- |
| (Rich plating medium for Streptomyces) | |
| Agar | 20 g |
| Distilled water | 1 liter |

Adjust to pH 7.5. Autoclave for 15 minutes at 121° C. Pour 30 to 35 ml into sterile plastic petri plates (100 by 15 mm).

PROCEDURES TO PRODUCE VIABLE PROTOPLASTS OF STREPTOMYCES AVERMITILIS STRAINS

A. Spores as Inocula

1. Spore preparations were prepared by standard procedures, the number of viable spores estimated by plating dilutions on germination agar, and aliquots frozen at −70° C. in 40% glycerol.

2. Before use, spore stocks were centrifuged at 1000 g for 10 minutes and resuspended in an equal volume of 0.85% saline.

3. Approximately $10^7$ spores were inoculated into 30 ml of Modified Yeast extract-Malt extract broth (YEME) medium containing 0.5% glycine (see below) in a 300 ml three or four-baffled flask.

B. Frozen Sonicated Mycelia as Inocula

1. Mycelial cultures of PGS-119 were grown in Trypticase Soy Broth (TSB) to a turbidity of 2 to 9 at 600 nm. The culture was homogenized 10 times with a glass tissue grinder.

2. The homogenized mycelia were diluted two-fold in TSB and 20 ml was added to a sterile polypropylene centrifuge tube. An ultrasonic probe was submerged to a depth of 1 to 2 cm into the liquid, and the sample sonicated at 50% intensity for 10 seconds. Sonication dispersed the mycelial masses into single or double cellular units which produced rapid exponential growth when subcultured.

3. Sonicated mycelial preparations were diluted to a final concentration of 40% glycerol, pipetted into vials, and frozen at −70° C.

4. Aliquots were thawed at room temperature as needed to inoculate into YEME medium as in Step A.3 above.

C. Colonies on Agar Medium as Inocula

1. Six mature colonies of PGS-119 growing on TSA or YPD-2 agars were introduced with a loop into 200 µl of sterile water in a microfuge tube.

2. The mycelial mixture was homogenized with disposable pestle.

3. The homogenized colonies were added to YEME medium as in Step A.3 above.

D. Preparation of Protoplasts from Mycelia Grown in Glycine

1. Cultures were incubated in a shaking water bath at 2° C. on setting 8 for Ca. 65 hours.

2. The mycelia were observed microscopically under 40× phase 2 magnification and harvested in a polypropylene centrifuge tube at about 1475 g for 10 minutes at 20° C.

3. The supernatant solution was discarded and the mycelial pellet was re-suspended in 10 ml Protoplast (P) Buffer (see below). The pellet was homogenized 5–10 times with a tissue grinder to disperse clumps.

4. The sample was centrigued at ca. 1000 g for 10 minutes. The supernatant solution was discarded and the pellet gently resuspended in 10 ml of P buffer.

5. The washing step above was repeated.

6. The mycelial pellet was resuspended in 10 ml of a 1.0 mg/ml fresh lysozyme solution in P buffer which had been filter-sterilized by passage through a 0.22 micron filter.

7. The mycelial mixture was incubated in a water bath at 37° C. with gentle shaking for 60 minutes. The samples were resuspended in the lysozyme solution every 15 minutes. Samples were observed microscopically under 40× phase illumination for the presence of protoplasts.

8. Mycelial preparations were triturated three times with a 5 ml pipet to free protoplasts from their cell walls.

9. Preparations were filtered through glass wool or non-absorbent cotton.

10. Protoplasts were sedimented by centrifuging at ca. 1000 g for 7 minutes, gently resuspended in 5 ml P buffer, and observed under 40× phase magnification.

11. The protoplasts were sedimented as above and resuspended in 1.0 ml P buffer. Dilutions of this suspension were made in P buffer and distilled water and plated on regeneration medium. Colonies which arose from protoplast preparations diluted in distilled water were assumed to be derived from incompletely or non-protoplasted mycelial units.

12. Protoplasts were frozen on ice in 200–300 µl aliquots at −70° C. They were removed from the ice 18–24 hours later.

FUSION OF PROTOPLASTS WITH POLYETHYLENE GLYCOL (PEG) 1000

1. All the experiments described herein were performed with a single lot of PEG 1000 (Sigma Chemical Co., St. Louis, Mo. 63178) which produced little apparent toxicity in our hands.

2. One (1.0) g aliquots of PEG were autoclaved in glass vials, 1.0 ml of P buffer was added, and the PEG was dissolved by heating the vial to 55° C. or the PEG was weighed, dissolved in P buffer and filter-sterilized just before use. PEG solutions were used at ambient temperatures.

3. Protoplasts were freshly prepared or thawed rapidly from −70° C. stocks under running water. Approximately equal numbers of protoplasts of each genotype were piperted gently into a polycarbonate centrifuge tube. For freshly-prepared protoplast preparations, turbidities were measured and several different concentrations were fused. The volume in each tube was adjusted to 5.0 ml with P buffer.

4. The fusion mixture was centrifuged at ca. 1000 g for 7 minutes.

5. The supernatant solution was decanted carefully. The protoplast pellet was gently resuspended to a final volume of 200 µl with P buffer.

6. Eight hundred (800) µl of 50% PEG was added rapidly to the fusion mixture. The preparation was mixed by drawing it up into a Pasteur pipet and expelling it again. The fusion was incubated for 2 minutes at room temperature. Nine (9) ml of P buffer was added to dilute the PEG. Additional fusions were performed serially so that incubation intervals were accurate.

7. The fusion mixtures were centrifuged as in Step 4 above, the supernatant solution decanted carefully and the fused, washed protoplasts were resuspended in 1.0 ml of P buffer.

8. The fusion mixture was serially diluted $10^{-1}$ and $10^{-2}$ in P buffer.

9. Fusions of each strain alone were performed in every experiment, and plated as controls.

10. Dilutions of each protoplast preparation (viable counts) were plated to determine numbers of viable regenerants of each strain used in the fusion procedure.

REGENERATION OF PROTOPLASTS

1. Protoplast suspensions, fusion mixtures, or self-fusions were diluted as appropriate in P buffer and plated in 100 µl aliquots onto regeneration agar media, using gentle spread technique. Spreading the fused protoplasts in soft agar overlays did not significantly improve their regeneration.

2. Where appropriate, the procedure described in D.11 above was used.

3. The regeneration plates were incubated right-side up in sealed plastic bags at 29°–30° C. and ca. 95% humidity.

4. For protoplast fusions in which spectinomycin-resistance was used as a dominant selectable marker, regenerating protoplasts were overlaid at 18 hours with 3.5 ml of 100 mcg/ml Spectinomycin in soft agar (see below) autoclaved and added at <45° C.

5. Protoplasts were incubated for 7–10 days.

GROWTH MEDIA, REGENERATION MEDIA, AND PROTOPLAST BUFFER Complete Regeneration Medium (Modified from Hopwood, et al. 1985. Genetic Manipulation of Streptomyces: A Laboratory Manual, p. 235)
Base solution:

| Sucrose | 205 g |
|---|---|
| $K_2SO_4$ | 0.25 g |
| $MgCl_2.6H_2O$ | 10.12 g |
| Glucose | 10 g |
| Difco Casaminoacids | 0.1 g |
| Difco Yeast Extract | 5.0 g |
| Difco Oatmeal Agar | 3.0 g |
| Difco Bacto Agar | 22.0 g |
| Distilled water to | 955 ml |

Autoclave for 25 minutes at 121° C. After autoclaving, add sterile stocks of:

| $KH_2PO_4$ (0.5%) | 10 ml |
|---|---|
| $CaCl_2.2H_2O$ | 5 ml |
| L-proline (20%) | 15 ml |
| MES buffer (1.0M) | 10 ml |
| Trace Element Solution* | 2.0 ml |
| NaOH (1N) | 3.0 ml |
| Adjust pH to 6.5; bring volume to 1 L. | |

*Trace Element Solution (per Liter):
| $ZnCl_2$ | 40 mg |
|---|---|
| $FeCl_3.6H_2O$ | 200 mg |
| $CuCl_2.2H_2O$ | 10 mg |
| $MnCl_2.4H_2O$ | 10 mg |
| $Na_2B_4O_7.10H_2O$ | 10 mg |
| $(NH_4)_6Mo_7O_{24}.4H_2O$ | 10 mg |

Spectinomycin soft Agar Overlays
Complete Regeneration Medium as above except:

| Agar | 4.10 g |
|---|---|

Autoclave as above. Cool to 55° C. Add 100 mg Spectinomycin. Aliquot in 5 ml volumes in capped culture tubes. Refrigerate. Autoclave again just before use.

Modified Protoplast (P) Buffer
Base solution:

| Sucrose | 205 g |
|---|---|
| $K_2SO_4$ | 0.25 g |
| $MgCl_2.6H_2O$ | 2.02 g |
| Distilled water to | 977 ml |

Autoclave for 25 minutes at 121° C. After autoclaving, add in order to sterile stocks of:

| $KH_2PO_4$ (0.5%) | 1 ml |
|---|---|
| Trace Element Solution* | 2 ml |
| $CaCl_2.2H_2O$ (3.68%) | 10 ml |
| MES Buffer (1.0M) | 10 ml |
| Adjust pH to 6.5; bring volume to 1 l. | |

*Trace Element solution recipe is above.

Modified Yeast Extract-Malt Extract (YEME) Medium
Base solution:

| Difco yeast extract | 3 g |
|---|---|
| Difco Bacto-peptone | 5 g |
| Difco Bacto malt extract broth | 3 g |
| Glucose | 10 g |
| Sucrose | 300 g |
| Distilled water to | 973 ml |

Autoclave for 25 minutes at 121° C. After autoclaving, add:

| $MgCl_2.6H_2O$ (2.5M) | 2 ml |
|---|---|
| Glycine (20%) | 25 ml |

Adjust volume to 1l.

Figure 1:
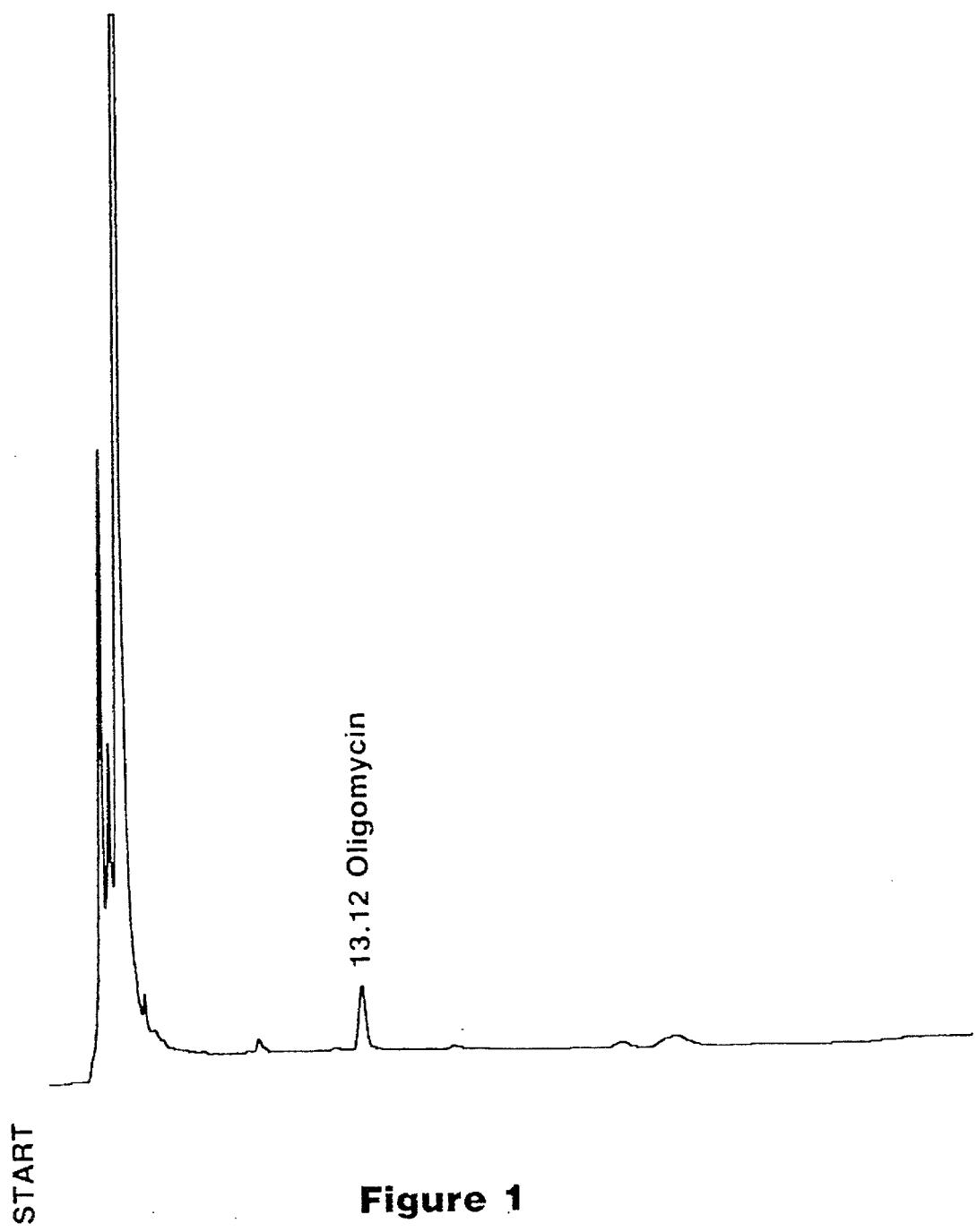
FIG. 1: UV Tracing (240 nm) versus time (minutes) of HPLC chromatograph of solvent fraction from solvent extraction of S. avermitilis I-3 (ATCC 53567) cells after growth on fatty acid-free medium (WPM SynA 40:40). Peak at 13.12 is oligomycin A.

The attached figures are accurate tracings of HPLC curves of the compounds indicated.

The compositions of media used in the following Examples are presented below. All molecular weight determinations were obtained by fast atom bombardment mass spectrometry performed on a VG Model 7070E mass spectrometer using a sample matrix of triethylene glycol with solid sodium chloride. $(M+Na)^+$ was determined. Electron impact mass spectrometry was performed using a VG Model 7070F mass spectrometer to provide m/e values only values for the principal fragments are recorded.

| AS-7 Medium | |
|---|---|
| | g/l |
| thinned starch[a] | 20 |
| Ardamine pH[b] | 5 |
| Pharmamedia[c] | 15 |
| $CaCO_3$ | 2 |

[a] Prepared by hydrolysis of starch by alpha-amylase from Bacillus licheniformis (available from Novo Enzymes, Wilton, CT and sold under the trademark "Termamyl") to a dextrose equivalent of 40% ± 5%.
[b] From Yeast Products, Inc., Clifton, NJ 07012
[c] From Traders Protein., Memphis, TN 38108

Adjust pH to 7.2 with NaOH.

| AP-5 Medium | |
|---|---|
| | g/l |
| thinned starch | 80 |
| Ardamine pH | 5 |
| $K_2HPO_4$ | 1 |
| $MgSO_4.7H_2O$ | 1 |
| NaCl | 1 |
| $CaCO_3$ | 7 |
| $FeSO_4.7H_2O$ | 0.01 |
| $MnCl_2.7H_2O$ | 0.001 |
| $ZnSO_4.7H_2O$ | 0.001 |
| P-2000 (antifoam) | 1 ml/l |

Adjust pH to 6.9 with 25% NaOH.

| WPM Syn A 40:40 | |
|---|---|
| | g/l distilled $H_2O$ |
| thinned starch | 40 |
| Potato soluble starch | 40 |
| glutamic acid | 1.0 |
| arginine | 0.168 |
| cystine | 0.084 |
| histidine | 0.069 |
| leucine | 0.798 |
| lysine | 0.297 |
| methionine | 0.108 |
| phenylalanine | 0.168 |
| threonine | 0.174 |
| tryptophan | 0.048 |
| tyrosine | 0.192 |
| $K_2HPO_4$ | 1.0 |
| $MgSO_4.7H_2O$ | 1.0 |
| NaCl | 1.0 |
| $CaCO_3$ | 3.5 |
| $FeSO_4.7H_2O$ | 0.01 |
| $MnCl_2.4H_2O$ | 0.001 |
| $ZnSO_4.7H_2O$ | 0.001 | pH adjusted to 6.8–7.0, stir 30 minutes at 121° C.

| WPM Syn B 40:40 | |
|---|---|
| | g/l distilled $H_2O$ |
| potato soluble starch | 40 |
| thinned starch | 40 |
| glutamic acid | 0.390 |
| arginine | 0.168 |
| cystine | 0.084 |
| histidine | 0.069 |
| lysine HCl | 0.297 |
| methionine | 0.108 |
| phenylalanine | 0.168 |
| threonine | 0.174 |
| tryptophan | 0.048 |
| tyrosine | 0.192 |
| $K_2HPO_4$ | 1 |
| $MgSO_4.7H_2O$ | 1 |
| NaCl | 1 |
| $CaCO_3$ | 3.5 |
| $FeSO_4.7H_2O$ | 0.01 |
| $MnCl_2.4H_2O$ | 0.001 |
| $ZnSO_4.7H_2O$ | 0.001 | pH adjusted to 6.8–7.0, stir 30 minutes at 121° C.

General High Performance Liquid Chromatography (HPLC) Procedures

Mobile Phase:
150 ml of water
70 ml of acetonitrile
bring to 1 liter with methanol
Column:
Ultrasphere ODS 25 cm (Beckman Instruments, Fullerton, Calif. 92634-3100)
flow: 0.75 ml/minute
detection: UV a 240 nm
attenuation: near 6
Sample diluent (D):
35 ml acetonitrile plus 390 ml methanol
Standards:

1. weigh 0.5 mg avermectin A2A into 10 ml flask and bring to volume with methanol
2. weigh 0.5 mg test product into 10 ml flask and bring to volume with methanol 1 and 2 are standard stock solutions; for standard solution to run:

take 100 ul (1) and 100 ul (2) into a vial
add 800 ul mobile phase
Samples:

1. Take 1 ml of well shaken broth; spin down
2. Remove as much supernatant as possible without disturbing pellet
3. Add 100 ul of HPLC water to the pellet and vortex mix to disperse
4. Add 2 ml diluent (D) and mix well
5. Filter the same and run on HPLC.

The natural avermectins were subjected to this HPLC chromatographic procedure and the retention time of the peaks of the individual avermectins divided by the retention time observed for the oligomycin A present and which serves as internal standard for a given HPLC determination. Oligomycin A is almost always observed by HPLC as by-product of *S. avermitilis* fermentations and is the only product seen on HPLC produced by the mutants described herein when they are cultured in a medium free of acids RCOOH wherein R is as defined herein or in medium free of compounds convertible to acids of the formula RCOOH wherein R is as defined herein. Typically, oligomycin A retention time is 12.5–14 minutes. The ratio of the retention times (RT) affords a more significant basis for comparing the identity and yields of avermectin products. The general order of appearance of the avermectin products on HPLC is B2, A2, B1 and A1 (FIG. 2).

| | RT/RT (oligomycin A) |
|---|---|
| Natural Avermectin | |
| B2b | 0.70 |
| B2a | 0.84 |
| A2b | 0.90 |
| A2a | 1.09 |
| B1b | 1.40 |
| B1a | 1.83 |
| A1b | 1.83 |
| A1a | 2.42 |
| Non-Natural Avermectin | |
| cyclopentyl B2 | 0.94 |
| cyclopentyl A2 | 1.23 |
| cyclopentyl B1 | 1.99 |
| cyclopentyl A1 | 2.62 |

Figure 2:
FIG. 2: UV Tracing (240 nm) of HPLC chromatograph of solvent fraction from solvent extraction of S. avermitilis MA4848 (ATCC 31272) cells after growth on fatty acid-free medium (WPM SynA 40:40). Products are natural avermectins.
Figure 3:
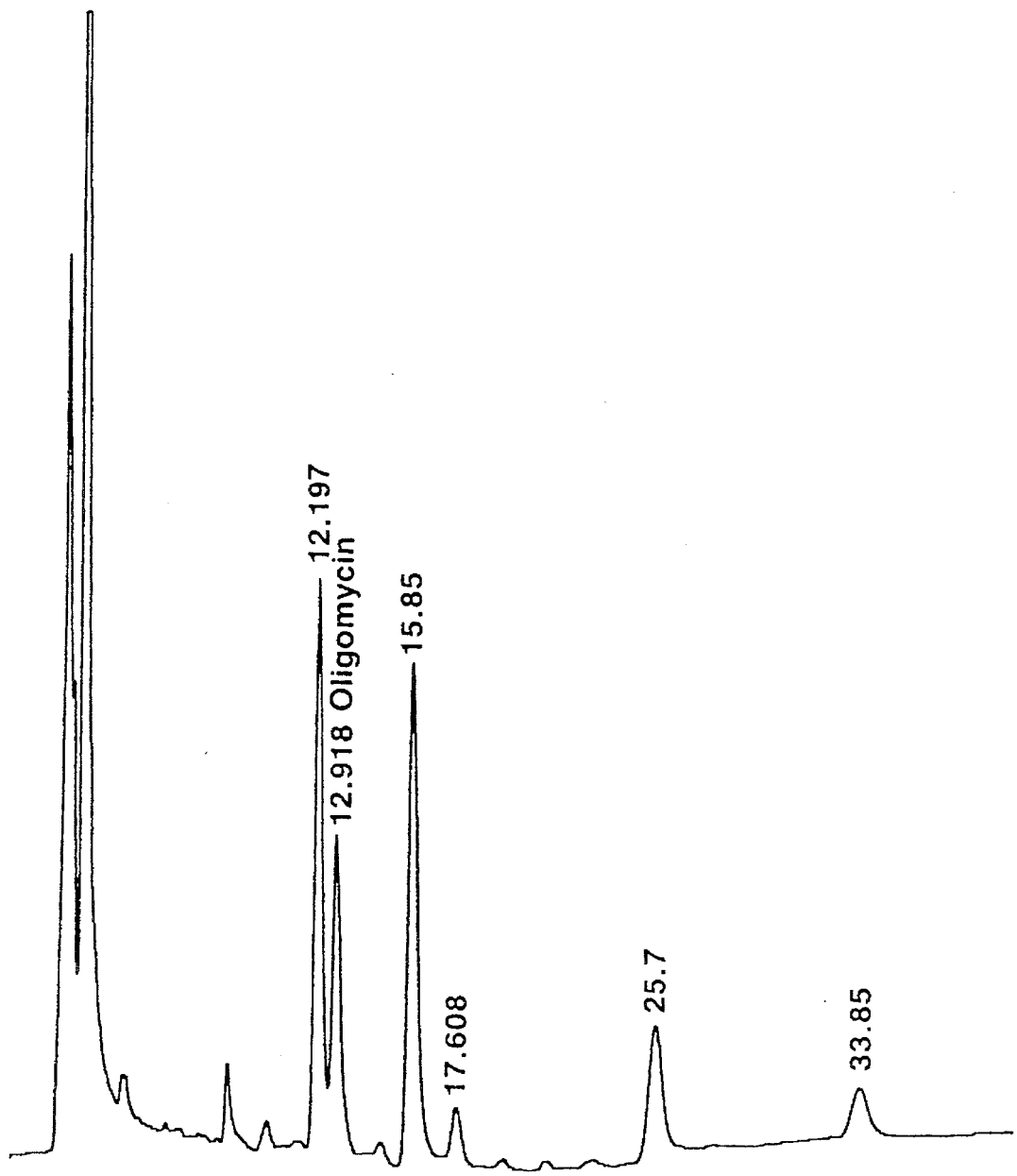
FIG. 3: UV Tracing (240 nm) of HPLC chromatograph of solvent fraction from solvent extraction of S. avermitilis I-3 (ATCC 53567) cells after growth on medium containing cyclopentylcarboxylic acid (see Example 1).

Ratios were determined from FIG. 2 for the natural avermectins (note that B1a and A1b are unresolved) and from FIG. 3 for the non-natural avermectins. Retention times vary 1–2 minutes on different days, with oligomycin A generally appearing near 12.5–14 minutes.

In the following examples the avermectins were determined by the above described HPLC procedure.

EXAMPLE 1

Cyclopentyl Avermectin A2

S. avermitilis I-3 (ATCC 53567) was cultured at 28°–30° C. in AS-7 medium with shaking for 24 hours. A 5 ml portion was used to inoculate a 500 ml flask containing 100 ml AS-7 medium and incubation was carried out under the same conditions for 24 hours; 1 ml of this culture was used to inoculate AP-5 medium (40 ml in 300 ml flask) to which 24 hours later was added 0.4 g/l of cyclopentane carboxylic acid (sodium salt). The product flasks were run with shaking at 28°–30° C. By 240 hours there was 35 mg/l cyclopentyl avermectin A2 produced while the corresponding natural A2a titer was 0. Other cyclopentyl avermectins were also produced.

EXAMPLE 2

Cyclopentyl Avermectin A2

A frozen vial of S. avermitilis HL-026 (ATCC 53568) was used to inoculate 100 ml of AS-7 medium in a 500 ml flask. Growth accompanied incubation at 28°–30° C. with shaking for 24 hours. A 1 ml aliquot was used to inoculate two additional 500 ml flasks containing 100 ml of AS-7 medium, and these latter flasks, after 18 hours incubation, were used to inoculate 10 liters of AP-5 (less NaCl) medium. After 24 hours of incubation at 28° C., 0.4 g/l of cyclopentane carboxylic acid was added to the medium. Agitation was such that dissolved oxygen was maintained above 20 percent of saturation. Cyclopentyl A2 titers at 120, 168, 216, 264 and 312 hours were 16, 40, 65, 88 and 110 mg/l, respectively. By way of contrast, the corresponding natural avermectin A2a titer was 0 (i.e., not detectable) in these samples.

EXAMPLE 3

Cyclopentyl Avermectin A2

In this experiment, the production medium was enriched and multiple additions of cyclopentane carboxylic acid were made to increase cyclopentyl avermectin titers. The conditions for inoculum development and fermentation were the same as those described in Example 2 except for the following: additional 5 g/l Ardamine pH (for a total of 10 g/l) was included in the AP-5 medium and 0.4, 0.2, and 0.2 g/l. of cyclopentane carboxylic acid were added at 30, 172 and 220, respectively. The cyclopentyl avermectin A2 titers were 1.2, 11, 78, 137 and 214 mg/l at 120, 168, 216, 264 and 312 hours, respectively.

EXAMPLE 4

Cyclopentyl Avermectins

A frozen vial of S. avermitilis HL-026 (ATCC 53568) was used to inoculate 100 ml of AS-7 medium in a 500 ml baffled flask which was incubated for 24–28 hours at 28°–30° C. Then, 1 ml of this culture was used to inoculate a 300 ml flask containing 40 ml of AP-5 (less NaCl but plus 0.6 g/l glutamic acid) medium. After 96 hours of incubation at 28°–30° C. with shaking, 0.4 g/l of cyclopentane carboxylic acid (sodium salt) was added. HPLC chromatography of a 216 hour sample showed cyclopentyl avermectins B2, A2, B1 and A1 present with retention times of 12.32, 15.86, 25.28 and 32.96 minutes, respectively.

EXAMPLE 5

Cyclopentyl Avermectin A2

In this example, S. avermitilis I-3 (ATCC 53567) and S. avermitilis HL-026 (ATCC 53568) were grown under identical conditions. Three media (AP-5, WPM Syn A 40:40, and WPM Syn B 40:40) were used. A frozen culture of each organism was used to inoculate 100 ml of AS-7 medium in 500 ml baffled flasks, which were incubated subsequently for 24–26 hours at 28°–30° C. Then, 1 ml of each culture was used to inoculate 300 ml flasks, each flask containing 40 ml of one of the three media. Duplicates of each flask were run. After 24 hours of incubation at 28° C. with shaking, each flask received 0.4 g/l of cyclopentylcarboxylic acid (sodium salt), and after a total of 192 hours of incubation, the titers of the principle product, cyclopentyl avermectin A2, were determined (Table I).

TABLE I

| Medium | Strain of S. avermitilis | Cyclopentyl avermectin A2 mg/l |
| --- | --- | --- |
| AP-5 | ATCC 53567 | 29 |
|  | ATCC 53568 | 67 |
| WPM Syn A 40:40 | ATCC 53567 | 35 |
|  | ATCC 53568 | 115 |
| WPM Syn B 40:40 | ATCC 53567 | 38 |
|  | ATCC 53568 | 36 |

EXAMPLE 6

Cyclohexyl Avermectins

In this example, 0.2 g/l of cyclohexane carboxylic acid was added at 96 hours instead of cyclopentane carboxylic acid, and all other conditions were the same as those described in Example 4. Four cyclohexyl avermectins were identified on the HPLC chromatogram of a 240 hour sample. The retention times for cyclohexyl avermectins B2, A2, B1 and A1 were 14.84, 19.26, 31.46 and 41.14 minutes, respectively.

EXAMPLE 7

3-Cyclohexenyl Avermectins

In this example, 0.2 g/l of 3-cyclohexene carboxylic acid was added at 96 hours instead of cyclopentane carboxylic acid, and all other conditions were the same as those described in Example 4. Several cyclohexenyl avermectins were identified on the HPLC chromatogram of a 312 hour sample. Their retention times are 12.88 (B2), 16.39 (A2), 27.37/28.36 (B1 isomers) and 35.80/37.13 (A1 isomers) minutes, respectively.

EXAMPLE 8

3-Thienyl Avermectins

In this example, 0.05 g/l of thiophene-3-carboxylic acid was added at 96 hours instead of cyclopentane carboxylic acid, and all other conditions were the same as those described in Example 4. Four 3-thienyl avermectins were identified on the HPLC chromatogram of a 312 hour sample. The retention times for 3-thienyl avermectins B2, A2, B1 and A1 were 6.96, 8.76, 13.8 and 23.5 minutes, respectively.

EXAMPLE 9

1-Methylthioethyl Avermectins

In this example, 0.4 and 0.2 g/l of 2-methylthiopropionic acid were added at 24 and 96 hours, respectively, instead of cyclopentane carboxylic acid, and all other conditions were the same as those described in Example 4. Two 1-methylthioethyl avermectins were identified on the HPLC chromatogram of a 240 hour sample. The retention times for 1-methylthioethyl avermectins A2 and B1 were 9.30 and 13.06 minutes, respectively. The peak, with an estimated retention time of about 7.2 minutes, emerging on the front shoulder of the 7.557 minute peak is believed to be the B2 compound, and the A1 compound is believed to be under the 17.22 minute peak.

EXAMPLE 10

2-pentyl Avermectins

In this example, 0.2 g/l of 2-methylvaleric acid was added at 96 hours instead of cyclopentane carboxylic acid, and all other conditions were the same as those described in Example 4. Four 2-pentyl avermectins were identified on the HPLC chromatogram of a 312 hour sample. The retention times for 2-pentyl avermectins B2, A2, B1 and A1 were 12.88, 16.58, 31.90 and 41.92 minutes, respectively.

EXAMPLE 11

1-Methyl-3-butenpyl Avermectins

In this example, 0.2 g/l of 2-methyl-4-pentenoic acid was added at 96 hours instead of cyclopentane carboxylic acid, and all other conditions were the same as those described in Example 4. Four 1-methyl-3-butenyl avermectins were identified on the HPLC chromatogram of a 312 hour sample. The retention times for 1-methyl-3-butenyl avermectins B2, A2, B1 and A1 were 11.13, 14.78, 22.10 and 28.92 minutes, respectively.

EXAMPLE 12

1-Methyl-1-butenyl Avermectins

In this example, 0.2 g/l of 2-methyl-2-pentenoic acid was added at 96 hours instead of cyclopentane carboxylic acid, and all other conditions were the same as those described in Example 4. Four 1-methyl-1-butenyl avermectins were identified on the HPLC chromatogram of a 312 hour sample. The retention times for 1-methyl-1-butenyl avermectins B2, A2, B1 and A1 were 11.59, 14.93, 25.29 and 33.18 minutes, respectively.

EXAMPLE 13

In this example, the use of the mutant to prepare the natural avermectins derived from L-valine in the absence of the avermectins derived from L-isoleucine is demonstrated. The contents of a frozen vial containing *S. avermitilis* I-3 (ATCC 53567) was transferred to a 500 ml baffled flask containing 100 ml of AS-7 medium. After approximately one day at 28°–30° C. with shaking (ca. 200 rpm), 1 ml of the culture is used to inoculate 40 ml of WPM Syn A 40:40 medium in a 300 ml flask, which is subsequently incubated at 28°–30° C. for 24 hours with shaking. At this time, 4 ml of a filter-sterilized solution of isobutyric acid (neutralized to pH 6–7 with NaOH), 4 mg/ml is added and incubation was continued as above for a total of 8 days. HPLC analysis showed 4 major peaks (excluding oligomycin). (In similar experiments with 2-methylbutyric acid replacing isobutryic acid, the complementary 4 peaks of avermectins derived from L-isoleucine were seen.

EXAMPLE 14

The procedure of Example 1 was repeated but substituting the primer compounds listed below for cyclopentane carboxylic acid. The avermectins (formula I compounds wherein $R^2$ is the oleandrose disaccharide moiety and R, $R^1$ and $R^3$ are as shown) identified from a given fermentation are also listed.

| | Primer | | Product: RT/RT (oligomycin A) | | | |
|---|---|---|---|---|---|---|
| Cpd | Compound | R | $B_2$ | $A_2$ | $B_1$ | $A_1$ |
| 1 | 2-methylvaleric acid | pent-2-yl | 1 | 1.287 | 2.478 | 3.255 |
| 2 | 2-methylpent-4-enoic acid | 4-penten-2-yl | 0.853 0.904 | 1.090 1.133 | 1.694 1.784 | 2.217 2.346 |
| 3 | 1-cyclohexene carboxylic acid | cyclohexen-1-yl | 0.785 | 1.021 | 1.665 | 2.179 |
| 4 | thiophene-2-carboxylic acid | thien-2-yl | | 0.694 | 1.143 | 1.499 |
| 5 | 3-furoic acid | 3-furyl | | 0.705 | 1.095 | |
| 6 | cyclobutane carboxylic acid | cyclobutyl | 0.728 | 0.933 | 1.546 | 2.027 |
| 7 | cyclopentane carboxylic acid | cyclopentyl | 0.960 | 1.236 | 1.970 | 2.568 |
| 8 | cyclohexane carboxylic acid | cyclohexyl | 1.206 | 1.565 | 2.556 | 3.343 |
| 9 | cycloheptane carboxylic acid | cycloheptyl | 1.465 | 1.923 | | |
| 10 | 3-cyclohexene-1-carboxylic acid | cyclohex-3-enyl | 1 | 1.273 | 2.125 | 2.780 |
| 11 | 2-methylthio-propionic acid | 1-methyl-thioethyl | 0.565 | 0.730 | 1.025 | 1.351 |
| 12 | thiophene-3-carboxyic acid | thien-3-yl | 0.539 | 0.639 | 1.069 | 1.388 |
| 13 | hydroxymethyl-cyclopentane | cyclopentyl | | identical to 7 | | |
| 14 | 3-thiophene carboxaldehyde | thien-3-yl | | identical to 12 | | |
| 15 | 3-cyclohexyl-propionic acid | cyclohexyl | | identical to 8 | | |
| 16 | 3-cyclopentyl-propionic acid | cyclopentyl | | identical to 7 | | |
| 17 | hydroxymethyl-cyclobutane | cyclobutyl | | identical to 6 | | |
| 18 | 3-cyclopentyl-1-propanol | cyclopentyl | | identical to 7 | | |
| 19 | cyclobutylmethyl-amine | cyclobutyl | | identical to 6 | | |
| 20 | ethyl cyclobutane-carboxylate | cyclobutyl | | identical to 6 | | |
| 21 | 2-(cyclobutyl-carbonyl)-propionic acid | cyclobutyl | | identical to 6 | | |
| 22 | ethyl 2-(3-thiophene carbonyl)-propionate | thien-3-yl | | identical to 12 | | |
| 23 | 1-methylcyclo-propane carboxylic acid | 1-methyl-cyclopropyl | | 1.236 | | |
| 24 | 2-methylpent-2-enoic acid | 2-penten-2-yl | 0.812 0.882 | 1.091 1.135 | 1.923 | 2.523 |
| 25 | 2-furoic acid | 2-furyl | | 0.709 | 1.146 | |

| Primer | | | Product: RT/RT (oligomycin A) | | | |
|---|---|---|---|---|---|---|
| Cpd | Compound | R | $B_2$ | $A_2$ | $B_1$ | $A_1$ |
| 26 | 5-methylthiophene-2-carboxylic acid | 5-methylthien-2-yl | 0.533 | | | 1.514 |
| 27 | 1-methylcyclopropane carboxylic acid | 1-methylcyclopropyl | | 1.236 | | |
| 28 | cyclopropane carboxylic acid | cyclopropyl | 0.802 | 1.048 | | 2.236 |

Other physico-chemical data for certain of the above compounds are presented below.

| Cpd | Physico-Chemical Data |
|---|---|
| 6 (A2) | white powder; m.p. 135–140° C.; molecular weight = 925; m/e 596, 454, 321, 303, 275, 237, 219, 209, 191, 179, 167, 145, 127, 113, 111, 95 and 87. |
| 6 (A1) | white powder; m.p. 120–124° C.; molecular weight = 907; m/e 578, 303, 275, 257, 219, 191, 167, 145, 127, 113, 111, 95 and 87. |
| 6 (B2) | white powder; m.p. 110–112° C.; molecular weight = 911; m/e 321, 303, 261, 257, 237, 219, 209, 191, 179, 167, 145, 127, 113, 111, 95 and 87. |
| 6 (B1) | white powder; m.p. 135–138° C.; molecular weight = 893; m/e 303, 261, 257, 219, 191, 167, 145, 127, 113, 111, 95 and 87. |
| 8 (A2) | white powder; m.p. 112–117° C.; molecular weight = 953; m/e 624, 482, 349, 349, 331, 275, 265, 247, 237, 219, 207, 195, 179, 145, 127, 113, 111, 95 and 87. |
| 10 (A2) | white powder; m.p. 131–135° C.; molecular weight = 951; m/e 624, 480, 347, 329, 275, 263, 245, 235, 217, 205, 193, 179, 145, 127, 113, 111, 95 and 87. |
| 12 (A2) | white powder; m.p. 167° C.; molecular weight = 953; m/e 349, 331, 275, 265, 257, 247, 237, 219, 195, 145, 127, 113, 95 and 87. |

EXAMPLE 15

Repetition of the procedure of Example 14, but using the primer compounds listed below affords the corresponding avermectin products: R avermectins A1, A2, B1 and B2 wherein R corresponds to the R group of the primer compound.

| Primer Compound | R |
|---|---|
| 2,3-dimethylbutyric | 1,2-dimethylpropyl |
| 2-methylhexanoic acid | hex-2-yl |
| 2-cyclopropyl propionic acid | 1-cyclopropylethyl |
| 4,4-difluorocyclohexane carboxylic acid | 4,4-difluorocyclohexyl |
| 4-methylenecyclohexane carboxylic acid | 4-methylenecyclohexyl |
| 3-methylcyclohexane carboxylic acid (cis/trans) | 2-methylcyclohexyl |
| 1-cyclopentene carboxylic acid | cyclopenten-1-yl |
| tetrahydropyran-4-carboxylic acid | tetrahydropyran-4-yl |
| 2-chlorothiophene-4-carboxylic acid | 2-chlorothien-4-yl |
| (S)-2-methylpentanoic acid | (S)-pent-2-yl |
| (R)-2-methylpentanoic acid | (R)-pent-2-yl |
| 2-methylcyclopropane carboxylic acid | 2-methylcyclopropyl |
| 2-methyl-4-methoxybutyric acid | 4-methoxybut-2-yl |
| tetrahydrothiophene-3-carboxylic acid | tetrahydrothien-3-yl |
| 3-methylcyclobutane carboxylic acid | 3-methylcyclobutyl |
| 3-fluorocyclobutane carboxylic acid | 3-fluorocyclobutyl |
| 3-methylene cyclobutane carboxylic acid | 3-methylenecyclobutyl |
| 2-methyl-4-methylthiobutanoic acid | 4-methylthiobut-2-yl |
| tetrahydrothiopyran-4-carboxylic acid | tetrahydrothiopyran-4-yl |
| 3-cyclopentenemethanol | cyclopent-3-enyl |

EXAMPLE 16

Cyclopentyl Avermectin A2 Recovery

This example is given to demonstrate a recovery process for the A2-like avermectins formed from the cyclopentanecarboxylic acid precursor. Whole broth (from a fermentation similar to that of Example 2) was filtered, and the mycelial cell mass was extracted twice with acetone (3 volumes). The acetone extract was concentrated to an aqueous oil, the oil extracted with methylene chloride and the methylene chloride solution concentrated to a dark brown oil. The dark brown oil was then dissolved in methanol/water (4:1) and the resulting solution extracted with hexane to remove fatty acids/lipids. Evaporation of the methanol/water afforded a light brown oil containing approximately 10% cyclopentyl avermectin A2 w/w. The crude avermectin oil was then diluted with chloroform (3 ml of $CHCl_3$ per g of oil), activated charcoal (0.35 g/g of oil) and silica gel (1 g/g of oil) were added, and the mixture stirred for an hour and then filtered. The filtrate was concentrated, and the resulting oil diluted with isopropyl ether (1 ml of IPE per g of oil). The resulting solution was then gradually dripped into a large volume of hexane (25 ml of hexane/g of oil), whereupon a white, crude avermectin powder precipitated. The first crop was isolated via filtration and the filtrate was then cooled to approximately 5° C. to precipitate out a second crop.

The crudes were further processed by preparative high performance liquid chromatography to obtain purified product. Crudes were dissolved (4.1 ml. solvent per gram of crude powder) in 25/25/25/50/0.125 IPE/$CH_3CN$/ethyl acetate/hexane/acetic acid. Samples were injected onto a 41.4 mm by 25 cm silica preparative column and eluted with the above solvent at 30 ml/minute and the product-containing peak collected. The collected fractions were concentrated and diluted with MeOH/$H_2O$ (86/14) such that 1 ml contained approximately 50 mg product. Samples were then injected on a C-18 preparative column (same dimensions as silica column) and eluted at 18–20 ml/minute with MeOH/$H_2O$ (275 ml $H_2O$ to 2 liters with MeOH). The fractions were again concentrated and passed over the C-18 prep column a second time. Evaporation of the product-containing fractions to dryness afforded pure title product.

The corresponding cyclopentyl avermectin B2, A1 and B1 are recovered by collecting the appropriate fractions from the above described HPLC steps.

EXAMPLE 17

S. avermitilis JC 923 (ATCC 53669) mycelium from a YPD-2 agar medium was used to inoculate 50 ml of AS-7 medium in a 300 ml baffled flask, which was maintained with shaking (220 rpm) at 30° C. for 24 hours. Then, each of two 300 ml flasks (no baffles) containing 50 ml of AP-5 medium was inoculated with one ml of the culture. One flask contained 2-methylbutyric acid (0.1%) and the other no 2-methylbutyric acid. Fermentation was carried out at 30° C. for 11 days with shaking. The contents of each flask was worked up in the same way. The whole broth was extracted with a four-fold volume excess of acetonitrile:methanol (810:75). After vigorous shaking to promote antibiotic extraction from the cells, the clarified supernatant was analyzed via HPLC for avermectins. When no fatty acid precursor was added, no detectable avermectins ("a" type) were found (sensitivity $\leq 0.20$ mg/L). In the presence of the 2-methylbutyric acid avermectins B2a, A2a, B1a, A1a were measured at 0.5, 1.3, 1.4 and 1.1 mg/L, respectively.

EXAMPLE 18

In this example, AP-5 production fermentations of S. avermitilis JC 923 (ATCC 53669) were prepared from AS-7 grown inocula as in Example 17. The primer compound 2-methylbutyric acid was present at 0.05% concentration. In this case, the unsupplemented control fermentation (no fatty acid precursor) gave values of 0.3, 0.9, <0.2 and <0.2 mg/L for avermectins B2a, A2a, B1a and A1a, respectively, whereas the results from the fatty acid supplemented fermentations were 2.8, 5.0, 4.5 and 2.3 mg/L, respectively.

EXAMPLE 19

In this example, AP-5 production fermentations of S. avermitilis JC 923 (ATCC 53669) were prepared from AS-7 inocula as in Example 18. In this example, 2-methylbutyric acid was added at 0.05% concentration 48 hours after the inoculation of the AP-5 medium, and cells were harvested by filtration, weighed (wet weight) and extracted with a four-fold weight excess of extraction solvent. This concentration step enable greater sensitivity in avermectin titer measurements over the previous cases in which whole broths were directly extracted. In the present example, levels of B2a, A2a, B1a, A1a of 2.5, 8.5, 4.5 and 3.5 mg/L were determined for the 2-methylbutyric acid supplemented fermentation, as compared to values of 0.3, 0.3, 0.3 and 0.1 for the unsupplemented control. These latter, low levels are presumably attributable to low levels of endogenous fatty acid compounds in the crude AP-5 production medium.

EXAMPLE 20

Fermentations were carried out as in Example 19, except that cyclopentane carboxylic acid at 0.045% concentration was substituted for the 2-methylbutyric acid supplementation. Cyclopentylavermectin A2 was determined to be present at 4 mg/L concentration.

EXAMPLE 21

Fermentations (16) of S. avermitilis PGS-119 (ATCC 53670) were carried out in 50 ml of AP-5 medium in 300 ml flasks (no baffles) incubated at 30° C. The medium was inoculated with one ml of a 24 hour culture of the strain in AS-7 medium, 30° C. incubation, 50 ml medium in 300 baffled flask. After 66 hours of growth in the AP-5 medium, isobutyric acid at a concentration of 0.1% was added to 8 of the flasks. Using the work-up procedure of Example 17, these supplemented flasks yielded concentrations of B2b, A2b, B1b and A1b equal to (average of two experiments) 5.6, 45, 45 and 68 mg/L, respectively. The unsupplemented cultures gave values of 0.5, 4.0, 4.5 and $\leq 8.5$ mg/L, respectively. In addition, for the latter fermentation, values of 1.1, 1.1, undetermined and <0.2 mg/L for the corresponding B2a, A2a, B1a and A1a avermectins were found.

EXAMPLE 22

In this example, four AP-5 fermentations of S. avermitilis PGS-119 (ATCC 53670) were carried out in 2 ml cultures in plastic tubes (15 ml). Inocula were prepared as described in Example 21 in AS-7 medium, at 30° with shaking of tubes maintained in a 30° slanted position. The fatty acid precursor, cyclohexane carboxylic acid (CHC), at a 0.045% concentration was added at 96 hours after AP-5 inoculation to two of the tubes. Four hundred hours following AP-5 inoculation, with 0.05 ml of the AS-7 culture, 8 ml of extraction solvent (acetonitrile:methanol (810:75)) was added to every tube and avermectin titers were determined in the supernatants by HPLC analysis as described in the text. For avermectins CHC-B2, CHC-A2, CHC-B1, CHC-A1, A2b, B1b, A1b, A2a and A1a, concentrations were equal to (average of two tubes) 3.5, 6.2, 3.0, 1.4, 0.2, 0.2, 0.4, 0.2, <0 2 mg/L, respectively. The corresponding values for the two fermentation tubes receiving no precursor acid were <0.2, <0.2, <0.2, <0.2, 4.2, 2.9, 9.3, 1.2, 0.3 mg/L, respectively. All other natural avermectins were essentially undetectable.

EXAMPLE 23

The procedure of Example 17 was repeated, but using the primer compound or precursor thereto listed below in place of 2-methylbutyric acid. In each instance, non-natural avermectins RA1, RA2, RB1 and RB2 wherein the 25-substituent corresponds to the R group of the primer compound or precursor thereto are produced.

Primer Compound cyclohexane carboxylic acid
cyclobutane carboxyic acid
2-methylpent-4-enoic acid
3-cyclohexene-1-carboxylic acid
2-methylthiopropionic acid
3-furoic acid
thiophene-3-carboxylic acid
1-methylcyclopropane carboxylic acid
3-cyclopentylpropionic acid
ethylcyclopentane carboxylate
tetrahydrothiophene-3-carboxylic acid
3-cyclopentenemethylamine
cyclobutylmethylamine
4-hydroxymethylcyclopentene
cyclopentane carboxamide
2-furaldehyde

EXAMPLE 24

Repetition of the procedure of Example 22, but using the primer compounds and precursors listed below in place of cyclohexane carboxylic acid affords the corresponding R-avermectins A1, A2, B1 and B2, respectively.

Primer Compound (S)-2-methylpentanoic acid
2-chlorothiophene-4-carboxylic acid
3-thiophenecarboxylic acid
2,3-dimethylbutyric acid
2-methylthiopropionic acid 2-furaldehyde
2-methyl-4-methoxybutyric acid
2-(cyclobutylcarbonyl)propionic acid

We claim:

1. A process for preparing an avermectin comprising culturing a mutant strain of *Streptomyces avermitilis* selected from the group consisting of a mutant lacking branched-chain 2-oxo acid dehydrogenase activity, a mutant lacking branched-chain amino acid transaminase activity and a mutant lacking both branched-chain 2-oxo acid dehydrogenase activity and branched-chain amino acid transaminase activity, under aerobic conditions in an aqueous nutrient medium comprising, in addition to an assimilable source of nitrogen, carbon and inorganic salts, (1) an acid of the formula RCOOH, or (2) a precursor of said acid having the formula R—$(CH_2)_n$—Z wherein n is 0, 2, 4, or 6; Z is —$CH_2OH$, —CHO, —$COOR^5$, —$CH_2NH_2$ or —$CONHR^6$ wherein $R^5$ is H or $(C_{1-6})$alkyl; $R^6$ is hydrogen, $(C_{1-4})$alkyl, —$CH(COOH)CH_2COOH$, —$CH(COOH)(CH_2)_2COOH$ or —$CH(COOH)(CH_2)_2SCH_3$, with the proviso that when a mutant lacking only branched-chain amino acid transaminase activity is cultured, the precursor is R—$(CH_2)_n$—Z as defined above or R—CO—Z, and wherein R is an alpha-branched chain group, the carbon atom thereof to which is attached the —COOH group is also attached to at least two other atoms or groups other than hydrogen, and Z is as defined above;

and recovering said avermectin.

2. A process according to claim 1 wherein R is other than isopropyl or (S)-sec-butyl.

3. A process according to claim 1 wherein the strain of *S. avermitilis* lacks branched-chain amino acid transaminase activity.

4. A process according to claim 3, wherein the *S. avermitilis* has all the identifying characteristics of ATCC 53669.

5. A process according to claim 1 wherein the strain of *S. avermitilis* lacks branched-chain 2-oxo acid dehydrogenase.

6. A process according to claim 5, wherein the *S. avermitilis* has all the identifying characteristics of ATCC 53567.

7. A process according to claim 5, wherein the *S. avermitilis* has all the identifying characteristics of ATCC 53568.

8. A process according to claim 1 wherein the strain of *S. avermitilis* lacks branched-chain amino acid transferase activity and branched-chain 2-oxo acid dehydrogenase activity.

9. A process according to claim 8, wherein the *S. avermitilis* has all the identifying characteristics of ATCC 53670.

10. A process according to claim 1 wherein R is an alpha-branched $C_3$–$C_8$ alkyl, $C_3$–$C_8$ alkenyl, $C_4$–$C_8$ alkynyl, $C_3$–$C_8$ alkoxyalkyl or $C_3$–$C_8$ alkylthioalkyl group; a $C_5$–$C_8$ cycloalkyl-alkyl group wherein the alkyl group is an alpha-branched $C_2$–$C_5$ alkyl group; a $C_3$–$C_8$ cycloalkyl or $C_5$–$C_8$ cycloalkenyl group, either of which may optionally be substituted by methylene or one or more $C_1$–$C_4$ alkyl groups or halo atoms; or a 3 to 6 membered oxygen or sulfur containing heterocyclic ring which may be saturated, or fully or partially unsaturated and which may optionally be substituted by one or more $C_1$–$C_4$ alkyl groups or halo atoms.

11. A process according to claim 10 wherein R is
cyclobutyl
cyclopentyl
cyclohexyl
cycloheptyl
2-methylcyclopropyl
3-cyclohexenyl
1-cyclopentenyl
1-cyclohexenyl
3-methylcyclohexyl (cis/trans)
4-methylenecyclohexyl
3-methylcyclobutyl
3-methylenecyclobutyl
3-cyclopentenyl
1-cyclopropylethyl
3-fluorocyclobutyl
4,4-difluorocyclohexyl
isopropyl
sec-butyl
2-pentyl
2,3-dimethylpropyl
2-hexyl
2-pent-4-enyl
2-methylthioethyl
S-2-methylpentyl
R-2-methylpentyl
2-thienyl
3-thienyl
4-tetrahydropyranyl
3-furyl
2-chlorothienyl
3-tetrahydrothienyl
4-methylthio-2-butyl
4-tetrahydrothiopyranyl
4-methoxy-2-butyl or
4-methylthio-2-butyl.

12. The process according to claim 11 wherein the strain of *S. avermitilis* is *S. avermitilis* ATCC 53567.

13. The process according to claim 11 wherein the strain of *S. avermitilis* is *S. avermitilis* ATCC 53568.

14. The process according to claim 11 wherein the strain of *S. avermitilis* is *S. avermitilis* ATCC 53669.

15. The process according to claim 11 wherein the strain of *S. avermitilis* is *S. avermitilis* ATCC 53670.

16. A process according to claim 10 wherein when R is an alpha-branched $C_3$–$C_8$ alkyl group, it is not isopropyl or (S)-sec-butyl.

17. The process according to claim 10 wherein the strain of *S. avermitilis* is *S. avermitilis* ATCC 53567.

18. The process according to claim 10 wherein the strain of *S. avermitilis* is *S. avermitilis* ATCC 53568.

19. The process according to claim 10 wherein the strain of *S. avermitilis* is *S. avermitilis* ATCC 53669.

20. The process according to claim 10 wherein the strain of *S. avermitilis* is *S. avermitilis* ATCC 53670.

21. A process according to claim 11 wherein said aqueous nutrient medium comprises R—COOH.

22. A process according to claim 11 wherein said aqueous nutrient medium comprises R—$(CH_2)_n$—Z.

23. A process according to claim 21 wherein R is cyclopentyl, cyclohexyl, 2-thienyl or 3-thienyl.

24. A process according to claim 21 wherein R is cyclohexyl.

25. A process according to claim 22 wherein R is cyclohexyl.

26. A process according to claim 1 wherein the avermectin is recovered in association with mycelium of the *Streptomyces avermitilis*.

27. A process according to claim 24 wherein the avermectin is recovered in association with mycelium of the *Streptomyces avermitilis*.

28. A process according to claim 25 wherein the avermectin is recovered in association with mycelium of the *Streptomyces avermitilis*.

* * * * *

UNITED STATES PATENT AND TRADEMARK OFFICE
CERTIFICATE OF CORRECTION

PATENT NO. : 5,583,015
DATED : December 10, 1996
INVENTOR(S) : Edmund W. Hafner et al.

It is certified that error appears in the above-identified patent and that said Letters Patent is hereby corrected as shown below:

Column 17, lines 50-51 - "2°C" should read -- 29°C --.

Signed and Sealed this

Fourth Day of March, 1997

Attest:

BRUCE LEHMAN

Attesting Officer

Commissioner of Patents and Trademarks